US006372911B1

(12) United States Patent
Barta et al.

(10) Patent No.: US 6,372,911 B1
(45) Date of Patent: Apr. 16, 2002

(54) PROCESS FOR PREPARING β-HYDROXYCARBAMATES AND THEIR CONVERSION TO OXAZOLIDINONES

(75) Inventors: Nancy Barta, Brighton, MI (US); Robert D. Larsen, Bridgewater, NJ (US); Daniel R. Sidler, Whitehouse Station, NJ (US); Steven A. Weissman, Short Hills, NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/482,799

(22) Filed: Jan. 13, 2000

Related U.S. Application Data
(60) Provisional application No. 60/119,234, filed on Feb. 9, 1999.

(51) Int. Cl.[7] .................. C07D 413/12; A61K 31/445
(52) U.S. Cl. ........................................ 546/208; 514/326
(58) Field of Search ........................... 514/326; 506/208

(56) References Cited

U.S. PATENT DOCUMENTS 5,028,340 A * 7/1991 Gallup ....................... 210/753
5,911,909 A * 6/1999 Coyle-Rees

FOREIGN PATENT DOCUMENTS

| WO | WO 97/44316 | 11/1997 |
| WO | WO 97/46516 | 12/1997 |
| WO | 98/57940 | * 12/1998 |

OTHER PUBLICATIONS

Jommi et al. "2–oxazolidiones as regioselective protection of . . . " Ca 107:6859 (1986).*
Cristiani et al. "Microbial corrosion prevention . . . " CA 129:279455 (1997).*
Smoot et al. "Chemistry a mordern course" p.413, (1975).*
G. Li et al., "N–Halocarbamate Salts Lead to More Efficient Catalytic Asymmetric Aminohydroxylation", Agnew. Chem. Int. Ed. Engl., 1996, vol. 35, No. 23/24, pp. 2813–2817.
E. Herranz et al., "Osmium–Catalyzed Vicinal Oxyamination of Olefins by N–Chloro–N–metallocarbamates", J. Org. Chem., 1980, vol. 45, pp. 2710–2713.
J. Rudolph et al., "Smaller Substitutes on Nitrogen Facilitate the Osmium–Catalyzed Asymmetric Aminohydration", Angew. Chem. Int. Engl., 1996, vol. 35, No. 23/24, pp. 2810–1812.
G. Li et al., "Catalytic Asymmetric Aminohydroxylation (AA) of Olefins", Angew. Chem. Int. Engl., 1996, vol. 35, No. 4, pp. 451–454.
G. Li et al., "Catalytic Asymmetric Aminohydroxylation Provides a Short Taxol Side–chain Synthesis", ACTA Chemica Scandinavica 1996, vol. 50, pp. 649–651.

M. Bruncko et al., "N–Bromoacetamide—A New Nitrogen Source for the Catalytic Asymmetric Aminohydroxylation of Olefins", Angew. Chem. Int. Ed. Engl., 1997, vol. 36, No. 13/14, pp. 1483–1486.
O. Reiser, "The Sharpless Asymmetric Aminohydroxylation of Olefins", Angew. Chem. Int. Ed. Engl., 1996, vol. 35, No. 12, pp. 1308–1309.
R. Angelaud et al., "Asymmetric Amino–Hydroxylation of Dienylsilanes. An Efficient Route to Amino–Cyclitols", Tetrahedron Letters, 1997, vol. 38, No. 8, pp. 1407–1410.
H. C. Kolb et al., "Asymmetric Dihydrolation", Transition Metals for Organic Synthesis, 1998, vol. 2, pp. 219–242.
B. Tao et al., "Reversal of Regioselection in the Asymmetric Aminohydroxylation of Cinnamates", Tetrahedron Letters, 1998, vol. 39, pp. 2507–2510.
K. L. Reddy et al., "N–Chloro–N–Sodio–2–Trimethylsilyl Ethyl Carbamate: A New Nitrogen Source for teh Catalytic Asymmetric Aminohydroxylation", Tetrahedron Letters, 1998, vol. 39, pp. 3667–3670.
K. L. Reddy et al., "From Styrenes to Enantiopure Alpha Arylglycines in Two Steps", J. Amer. Chem. Soc., 1998, vol. 120, pp. 1207–1217.
D. J. Ager et al., "1,2–Amino Alcohols and Their Heterocyclic Derivatives as Chiral Auxiliaries in Asymmetric Synthesis", Chem. Rev., 1996, vol. 96, pp. 835–875.
G. Li et al., "New Synthesis of Evans chiral oxazolidinones by using Sharpless AA reaction", J. Chem. Soc., 1998, Perkin Trans. vol. 1, pp. 1753–1754.
M. E. Dyen et al., "2–Oxazolidinones", Chem. Rev., 1967, vol. 67, pp. 197–246.
H. C. Kolb et al., "Asymmetric Aminohydroxylation", Transition Metals for Organic Synthesis, 1998 vol. 2, pp. 243–260.

* cited by examiner

*Primary Examiner*—Ceila Chang
(74) *Attorney, Agent, or Firm*—Baerbel R. Brown; Catherine D. Fitch; Kenneth R. Walton

(57) ABSTRACT

A process for preparing a β-hydroxy carbamate product is disclosed. The process comprises reacting an olefin compound containing at least one carbon-carbon double bond with a carbamate in an aqueous solvent and in the presence of a base, an osmium catalyst, a co-oxidant selected from a halohydantoin, a haloisocyanuric acid, and an alkali metal salt of a haloisocyanuric acid, and optionally an asymmetric ligand, to form a reaction mixture containing the β-hydroxy carbamate product. The process optionally further comprises treating the β-hydroxy carbamate product with additional base to form an oxazolidinone. The oxazolidinones are useful as chiral auxiliary agents and as intermediates for the formation of pharmaceutically active substances such as alpha 1 a adrenergic receptor antagonists. A process for preparing nitrogen-functionalized derivatives of the oxazolidinones is also disclosed.

38 Claims, No Drawings

PROCESS FOR PREPARING β-HYDROXYCARBAMATES AND THEIR CONVERSION TO OXAZOLIDINONES

CROSS-REFERENCE TO RELATED APPLICATIONS

This patent application claims the benefit of U.S. provisional patent application Ser. No. 60/119,234, filed Feb. 9, 1999, the disclosure of which is herein incorporated by reference in its entirety.

FIELD OF THE INVENTION

The invention relates to processes for preparing β-hydroxy carbamates and oxazolidinones. More particularly, the invention is directed to the aminohydroxylation of olefins by reacting the olefins with a carbamate in aqueous solvent in the presence of a base, an osmium catalyst, a co-oxidant selected from a halohydantoin and a haloisocyanuric acid or its alkali metal salt, and optionally an asymmetric ligand. The invention is further directed to conversion of β-hydroxy carbamates to oxazolidinones which are useful as chiral auxiliary agents and as intermediates for the formation of pharmaceutically active substances such as alpha 1 a adrenergic receptor antagonists. The invention is also directed to a process for preparing nitrogen-functionalized derivatives of the oxazolidinones.

References are made in this application to various publications, the disclosures of which are hereby incorporated by reference in their entireties, in order to more fully describe the state of the art to which this invention pertains.

BACKGROUND OF THE INVENTION

Olefins have been converted to β-hydroxy carbamates by reaction with carbamates using t-butyl hypochlorite as a co-oxidant. WO 97/46516, for example, discloses the conversion of olefins to asymmetric β-hydroxy carbamate products by the asymmetric addition of a carbamoyl radical and a hydroxyl radical to the double bond, wherein the olefin is reacted with a carbamate in a reaction solution containing an osmium catalyst, NaOH, t-butyl hypochlorite, a chiral ligand, and a solvent having an organic component and an aqueous component. The use of t-butyl hypochlorite in aminohydroxylations is problematic, because it is relatively expensive, can explode at room temperature, and is light sensitive resulting in a relatively short shelf life. To minimize safety hazards, t-butyl hypochlorite is generally used in solution form (typically an aqueous solution), which can present handling problems in large scale operations.

Methods for preparing 2-oxazolidinones are described in M. E. Dyen et al., Chem. Rev., 67, 197 (1967) and L. Ager et al., Chem. Rev., 96, 835 (1996). The compounds can be prepared, for example, by reaction of β-aminoalcohols with phosgene. As another example, asymmetric 2-oxazolidinones have been prepared from commercially available amino acids (e.g., phenylalanine, valine, phenylglycine, norephedine and t-leucine) by reducing the acids to their corresponding aminoalcohols using reducing agents such as sodium borohydride-sulfuric acid, $NaBH_4$, $LiAlH_4$ and the like, and then reacting the aminoalcohols with phosgene or with a dialkylcarbonate. Thus, L-phenylalanine can be reduced with borane, followed by reaction with diethylcarbonate to produce an enantiomerically pure 4-benzyl-2-oxazolidinone.

SUMMARY OF THE INVENTION

The present invention is an aminohydroxylation process in which an olefin compound is reacted with a carbamate in the presence of a co-oxidant selected from a halohydantoin (e.g., 1,3-dichloro-5,5-dimethylhydantoin), a haloisocyanuric acid, and an alkali metal salt of a haloisocyanuric acid (e.g., sodium dichloroisocyanurate). These co-oxidants are highly effective, with the process typically characterized by higher enantioselectivity, better yields and/or shorter reaction times than analogous hypochlorite processes. The use of a hydantoin provides other significant benefits over known hypochlorite-based aminohydroxylation processes in that the hydantoins (i) are typically stable solids which present essentially no explosion hazards, (ii) can be safely handled in solid form which permits easy scale-up of the reaction, and (iii) are comparatively inexpensive.

More particularly, the invention is a process for preparing a β-hydroxy carbamate product which comprises reacting an olefin compound containing at least one carbon-carbon double bond with a carbamate in an aqueous solvent and in the presence of a base, an osmium catalyst, a co-oxidant, and optionally an asymmetric ligand, to form a reaction mixture containing the β-hydroxy carbamate product; wherein the co-oxidant is (1) a hydantoin is of Formula (Ia):

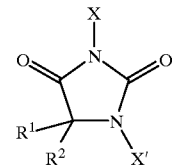

(Ia)

wherein X and X' are each independently H, Cl, or Br, and at least one of X and X' is Cl or Br; $R^1$ and $R^2$ are each independently selected from H, $C_1$–$C_6$ alkyl, $C_3$–$C_8$ cycloalkyl, $C_4$–$C_{20}$ alkylcycloalkyl, and $C_4$–$C_{20}$ cycloalkyl-alkyl; or (2) an isocyanuric acid of Formula (Ib):

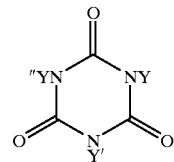

(Ib)

or an alkali metal salt thereof; wherein Y, Y' and Y" are each independently H, Cl, or Br, and at least one of Y, Y' and Y" is Cl or Br.

One embodiment of the invention is the process as set forth in the preceding paragraph, wherein the starting olefin compound is characterized by the absence of a $C_2$ axis of symmetry parallel to the double bond, the reaction mixture includes the asymmetric ligand, and the product is an asymmetric β-hydroxy carbamate.

Another embodiment of the invention is the process as set forth in either of the two preceding paragraphs, farther comprising treating the reaction mixture with additional base to form at least one oxazolidinone; and optionally further comprising recovering the oxazolidinone from the reaction mixture. In an aspect of this embodiment, the additional base used to form the oxazolidinone is an alkali metal carbonate, and the oxazolidinone is recovered by acidifying the reaction mixture containing the oxazolidinone, neutralizing the acidified mixture with base, and extracting the oxazolidinone with organic solvent.

Still another embodiment of the invention is a process for reacting an amine with the oxazoldinone prepared and recovered as described above to obtain a coupled amine product.

These and other embodiments, aspects and features of the present invention are either further described in or will be apparent from the ensuing description, examples and appended claims.

DETAILED DESCRIPTION OF THE INVENTION

The present invention is a process for preparing a β-hydroxy carbamate product which comprises reacting an olefin compound containing at least one carbon-carbon double bond with a carbamate in an aqueous solvent and in the presence, of a base, an osmium catalyst, a co-oxidant selected from a halohydantoin, a haloisocyanuric acid, and an alkali metal salt of a haloisocyanuric acid, and optionally an asymmetric ligand to form a reaction mixture containing the β-hydroxy carbamate product.

The hydantoin employed in the process of the invention is a halohydantoin of Formula (Ia):

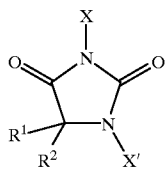

(Ia)

wherein X and X' are each independently H, Cl, or Br, and at least one of X and X' is Cl or Br; $R^1$ and $R^2$ are each independently selected from H, $C_1$–$C_6$ alkyl, $C_3$–$C_8$ cycloalkyl, $C_4$–$C_{20}$ alkylcycloalkyl, and $C_4$–$C_{20}$ cycloalkylalkyl. In one embodiment, $R^1$ and $R^2$ are each independently selected from H and $C_1$–$C_6$ alkyl (e.g., H and $C_1$–$C_4$ alkyl), and X and X' are as heretofore defined. In a second embodiment, X and X' are both Cl, and $R^1$ and $R^2$ are as heretofore defined. In an aspect of the second embodiment, X and X' are both Cl and $R^1$ and $R^2$ are each independently selected from $C_1$–$C_4$ alkyl. In a third embodiment, one of X and X' is Cl, the other of X and X' is Br, and $R^1$ and $R^2$ are as heretofore defined. A suitable hydantoin is, for example, 1,3-dichloro-5,5-dimethylhydantoin; i.e., X and X' are both Cl, and $R^1$ and $R^2$ are both methyl. Other suitable hydantoins include, but are not limited to, 1,3-dibromo-5,5-dimethylhydantoin, 1-bromo-3-chloro-5,5-dimethylhydantoin, 3-bromo-1-chloro-5,5-dimethylhydantoin, and 1,3-dichloro-5-methyl-5-isopropylhydantoin.

The isocyanuric acid employed in the process of the invention is a haloisocyanuric acid of Formula (Ib):

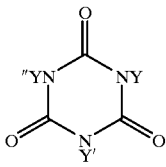

(Ib)

or an alkali metal salt thereof; wherein Y, Y' and Y" are each independently H, Cl, or Br, and at least one of Y, Y' and Y" is Cl or Br. In one embodiment, no more than one of Y, Y' and Y" is H, and, in an aspect of this embodiment, at least two of Y, Y' and Y" are Cl. Suitable isocyanuric acids include, but are not limited to, dichloroisocyanuric acid and trichloroisocyanuric acid.

The alkali metal salts of the haloisocyanuric acid of Formula (Ib) may also be employed as the co-oxidant. A class of the salts within this group is the sodium salts. Suitable salts include, but are not limited to, the sodium salt of dichloroisocyanuric acid.

The olefin compound employed in the process of the invention contains at least one carbon-carbon double bond. The olefin compound suitably has from 2 to about 40 carbon atoms, and typically has from 2 to about 30 carbon atoms (e.g., from 2 to about 24 carbon atoms).

In one embodiment, the olefin compound is a hydrocarbon or a substituted hydrocarbon containing at least one carbon-carbon double bond. The hydrocarbon or substituted hydrocarbon suitably has from 2 to about 40 carbon atoms, and typically has from 2 to about 30 carbon atoms (e.g., from 2 to about 24 carbon atoms). The term "hydrocarbon" means a compound consisting of carbon and hydrogen, which is entirely aliphatic, entirely alicyclic, or partly aliphatic and partly alicyclic, and which optionally also contains or incorporates within its structure one or more aromatic (i.e., phenyl or naphthyl) moieties. It is of course understood that in this context the hydrocarbon contains at least one non-aromatic double bond. The term "substituted hydrocarbon" means a hydrocarbon as just defined, wherein (i) one or more hydrogen atoms have been replaced by one or more heteroatom-containing (e.g., halogen-, N—, O—, and/or S-containing) substituents such as halogen, hydroxy (—OH), mercapto (—SH), oxo (=O), alkoxy (—O-alkyl), primary amino (—NH$_2$), N-alkylamino (—NH-alkyl), N,N-dialkylamino (—N(alkyl)$_2$), carboxamido (—C(=O)NH$_2$), carboxy (—COOH), alkoxycarbonyl (—C(=O)O-alkyl), alkylcarbonyl (—C(=O)-alkyl), formyl (—CHO), nitro (—NO$_2$), cyano (—CN), and the like, wherein alkyl means a linear or branched alkyl group; or (ii) from one or to no more than half (i.e., no more than 1 in 2, and typically no more than 1 in 3; e.g., no more than 1 in 4 or no more than 1 in 5) of the carbon atoms (whether aliphatic, alicyclic, or aromatic) have been replaced by one or more heteroatoms such as nitrogen, oxygen, or sulfur; or (iii) a combination of carbon atoms and hydrogen atoms have been replaced in accordance with (i) and (ii). The degree of substitution in the substituted hydrocarbon can vary from a low level of substitution such that the substituted hydrocarbon is predominantly hydrocarbon in character to a high level such that the properties of the substituted hydrocarbon differ substantially from its hydrocarbon counterpart.

In another embodiment, the olefin compound is an acrylic ester of Formula (II):

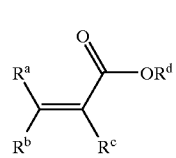

(II)

wherein $R^a$, $R^b$, and $R^c$ are each independently hydrogen, hydrocarbyl or substituted hydrocarbyl (suitably $C_1$–$C_{18}$ hydrocarbyl or substituted $C_1$–$C_{18}$ hydrocarbyl; e.g., $C_1$–$C_{12}$ hydrocarbyl or substituted $C_1$–$C_{12}$ hydrocarbyl), and $R^d$ is hydrocarbyl or substituted hydrocarbyl (suitably $C_1$–$C_8$ hydrocarbyl or substituted $C_1$–$C_8$ hydrocarbyl, e.g., $C_1$–$C_6$ hydrocarbyl or substituted $C_1$–$C_6$ hydrocarbyl).

In still another embodiment, and from the perspective of the carbon-carbon double bond, the olefin compound is a mono-substituted olefin, 1,1-disubstituted olefin, cis-disubstituted olefin, trans-disubstituted olefin, tri-substituted olefin, or tetra-substituted olefin, wherein each substituent is selected from hydrocarbyl, substituted hydrocarbyl, carboxylic acid hydrocarbyl ester, and carboxylic acid substituted hydrocarbyl ester. In one aspect of this embodiment, the olefin compound is selected from the group consisting of mono-substituted, 1,1-disubstituted, trans-disubstituted, and trisubstituted olefins, wherein each substituent is independently $C_1$–$C_{18}$ hydrocarbyl, substituted $C_1$–$C_{18}$ hydrocarbyl, carboxylic acid $C_1$–$C_8$ hydrocarbyl ester, or carboxylic acid substituted. $C_1$–$C_8$ hydrocarbyl ester. In another aspect, the olefin compound is selected from the group consisting of mono-substituted, 1,1-disubstituted, trans-disubstituted, and trisubstituted olefins (and is, for example, trans-disubstituted), wherein one substituent is selected from carboxylic acid $C_1$–$C_8$ hydrocarbyl ester and carboxylic acid substituted $C_1$–$C_8$ hydrocarbyl ester, and the remaining substituent on the 1,1- and the trans-disubstituted olefins and the remaining substituents trisubstituted olefin are independently selected from hydrocarbyl and substituted hydrocarbyl, preferably from $C_1$–$C_{18}$ hydrocarbyl and substituted $C_1$–$C_{18}$ hydrocarbyl. Carboxylic acid hydrocarbyl ester can alternatively be referred to as hydrocarbyl carboxylate, and carboxylic acid substituted hydrocarbyl ester as substituted hydrocarbyl carboxylate.

In yet another embodiment, the olefin compound is a compound of formula (III):

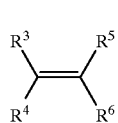

(III)

wherein $R^3$, $R^4$, $R^5$ and $R^6$ are each independently selected from hydrogen, $C_1$–$C_{12}$ alkyl, $C_2$–$C_{12}$ alkenyl, $C_3$–$C_8$ cycloalkyl, $C_4$–$C_{20}$ alkylcycloalkyl, $C_4$–$C_{20}$ cycloalkyl-alkyl, $C_5$–$C_8$ cycloalkenyl, $C_6$–$C_{20}$ alkylcycloalkenyl, $C_6$–$C_{20}$ cycloalkenylalkyl, $C_6$–$C_{10}$ aryl, $C_7$–$C_{20}$ alkylaryl, $C_8$–$C_{20}$ alkenylaryl, $C_7$–$C_{20}$ arylalkyl, heterocyclic, carboxylic acid $C_1$–$C_8$ alkyl ester, substituted $C_1$–$C_{12}$ alkyl, substituted $C_2$–$C_{12}$ alkenyl, substituted $C_3$–$C_8$ cycloalkyl, substituted $C_4$–$C_{20}$ alkylcycloalkyl, substituted $C_4$–$C_{20}$ cycloalkyl-alkyl, substituted $C_5$–$C_8$ cycloalkenyl, substituted $C_6$–$C_{20}$ alkylcycloalkenyl, substituted $C_6$–$C_{20}$ cycloalkenylalkyl, substituted $C_6$–$C_{10}$ aryl, substituted $C_7$–$C_{20}$ alkylaryl, substituted $C_8$–$C_{20}$ alkenylaryl, substituted $C_7$–$C_{20}$ arylalkyl, substituted heterocyclic, and carboxylic acid substituted $C_1$–$C_8$ alkyl ester, wherein the substituents therefor are independently selected from halogen, hydroxy, $(CH_2)_{0-2}OR^7$, nitro, cyano, $(CH_2)_{0-2}COOR^7$, $COR^7$, $(CH_2)_{0-2}CON(R^7)_2$, and $N(R^7)_2$; or $R^3$ and $R^4$ together with the carbon atom to which they are attached form a 5- to 10-membered monocyclic or bicyclic saturated or unsaturated carbocyclic ring system which is optionally substituted with one or more of $C_1$–$C_8$ alkyl, halogen, hydroxy, and $(CH_2)_{0-2}OR^7$; and $R^5$ and $R^6$ are as defined above; or $R^3$ and $R^5$ together with each of the carbon atoms of the carbon-carbon double bond form a 5- to 10-membered monocyclic or bicyclic unsaturated carbocyclic ring system which is optionally substituted with one or more of $C_1$–$C_8$ alkyl, halogen, hydroxy, and $(CH_2)_{0-2}OR^7$; and $R^4$ and $R^6$ are each independently selected from hydrogen, $C_1$–$C_{12}$ alkyl, $C_2$–$C_{12}$ alkenyl, $C_3$–$C_8$ cycloalkyl, $C_4$–$C_{20}$ alkylcycloalkyl, $C_5$–$C_8$ cycloalkenyl, $C_6$–$C_{20}$ alkylcycloalkenyl, $C_6$–$C_{10}$ aryl, $C_7$–$C_{20}$ alkylaryl, $C_8$–$C_{20}$ alkenylaryl, $C_7$–$C_{20}$ arylalkyl, heterocyclic, carboxylic acid $C_1$–$C_8$ alkyl ester, substituted $C_1$–$C_{12}$ alkyl, substituted $C_2$–$C_{12}$ alkenyl, substituted $C_3$–$C_8$ cycloalkyl, substituted $C_4$–$C_{20}$ alkylcycloalkyl, substituted $C_5$–$C_8$ cycloalkenyl, substituted $C_6$–$C_{20}$ alkylcycloalkenyl, substituted $C_6$–$C_{10}$ aryl, substituted $C_7$–$C_{20}$ alkylaryl, substituted $C_8$–$C_{20}$ alkenylaryl, substituted $C_7$–$C_{20}$ arylalkyl, substituted heterocyclic, and carboxylic acid substituted $C_1$–$C_8$ alkyl ester, wherein the substituents therefor are independently selected from halogen, hydroxy, $(CH_2)_{0-2}OR^7$, nitro, cyano, $(CH_2)_{0-2}COOR^7$, $COR^7$, $(CH_2)_{0-2}CON(R^7)_2$, and $N(R^7)_2$; or $R^3$ and $R^4$ together with the carbon atom to which they are attached form one 5- to 10-membered monocyclic or bicyclic saturated or unsaturated carbocyclic ring system; and $R^5$ and $R^6$ together with the carbon atom to which they are attached form a second 5 to 10 membered monocyclic or bicyclic saturated or unsaturated carbocyclic ring system, wherein each ring system is optionally substituted with one or more of $C_1$–$C_8$ alkyl, halogen, hydroxy, and $(CH_2)_{0-2}OR^7$; and $R^7$ is $C_1$–$C_6$ alkyl.

A first aspect of the olefin compound of Formula (III) is a compound wherein $R^3$, $R^4$, $R^5$ and $R^6$ are each independently selected from hydrogen, $C_1$–$C_6$ alkyl, $C_2$–$C_8$ alkenyl, $C_3$–$C_6$ cycloalkyl, $C_6$–$C_{14}$ alkyl-cycloalkyl, $C_6$–$C_{14}$ cycloalkyl-alkyl, $C_5$–$C_7$ cycloalkenyl, $C_6$–$C_{16}$ alkylcycloalkenyl, $C_6$–$C_{16}$ cycloalkenylalkyl, phenyl, $C_7$–$C_{20}$ alkylphenyl, $C_7$–$C_{12}$ phenylalkyl, carboxylic acid $C_1$–$C_6$ alkyl ester, substituted $C_1$–$C_6$ alkyl, substituted $C_2$–$C_8$ alkenyl, substituted $C_3$–$C_6$ cycloalkyl, substituted $C_6$–$C_{14}$ alkyl-cycloalkyl, substituted $C_6$–$C_{14}$ cycloalkyl-alkyl, substituted $C_5$–$C_7$ cycloalkenyl, substituted $C_6$–$C_{16}$ alkylcycloalkenyl, substituted $C_6$–$C_{16}$ cycloalkenylalkyl, substituted phenyl, substituted $C_7$–$C_{20}$ alkylphenyl, substituted $C_7$–$C_{12}$ phenylalkyl, carboxylic acid substituted $C_1$–$C_6$ alkyl ester, wherein the substituents therefor are independently selected from halogen, hydroxy, $(CH_2)_{0-2}OR^7$, nitro, cyano, $(CH_2)_{0-2}COOR^7$, $COR^7$, $(CH_2)_{0-2}CON(R^7)_2$, and $N(R^7)_2$.

A second aspect of the olefin compound of Formula (III) is a compound in which two of $R^3$, $R^4$, $R^5$ and $R^6$ are hydrogen, and the other two of $R^3$, $R^4$, $R^5$ and $R^6$ are not hydrogen (i.e., the two substituents are selected from the groups set forth in the preceding sentence except for hydrogen); and all else is as defined above in the first aspect.

A third aspect of the olefin compound of Formula (III) is a trans-disubstituted olefin compound, wherein $R^3$ and $R^6$ are hydrogen;

$R^4$ and $R^5$ are each independently selected from $C_1$–$C_{12}$ alkyl, $C_2$–$C_{12}$ alkenyl, $C_3$–$C_8$ cycloalkyl, $C_4$–$C_{20}$ alkylcycloalkyl, $C_5$–$C_8$ cycloalkenyl, $C_6$–$C_{20}$ alkylcycloalkenyl, $C_6$–$C_{10}$ aryl, $C_7$–$C_{20}$ alkylaryl, $C_8$–$C_{20}$ alkenylaryl, $C_7$–$C_{20}$ arylalkyl, heterocyclic, carboxylic acid $C_1$–$C_8$ alkyl ester, substituted $C_1$–$C_{12}$ alkyl, substituted $C_2$–$C_{12}$ alkenyl, substituted $C_3$–$C_8$ cycloalkyl, substituted $C_4$–$C_{20}$ alkylcycloalkyl, substituted $C_5$–$C_8$ cycloalkenyl, substituted $C_6$–$C_{20}$ alkylcycloalkenyl, substituted $C_6$–$C_{10}$ aryl, substituted C₇–C₂₀ alkylaryl, substituted C₈–C₂₀ alkenylaryl, substituted C₇–C₂₀ arylalkyl, substituted heterocyclic, and carboxylic acid substituted C₁–C₈ alkyl ester, wherein the substituents therefor are independently selected from halogen, hydroxy, (CH₂)₀₋₂OR⁷, nitro, cyano, (CH₂)₀₋₂COOR⁷, COR⁷, (CH₂)₀₋₂CON(R⁷)₂, and N(R⁷)₂; and N(R⁷)₂; and R⁷ is C₁ to C₆ alkyl.

Another aspect of the olefin compound of Formula (III) is a compound in which R⁷ is C₁–C₄ alkyl (e.g., R⁷ is methyl or ethyl); and all other variables are as originally defined above or as defined in any one of the preceding aspects.

Still another aspect of the olefin compound of Formula (III) is a compound wherein one of R³ and R⁴ is hydrogen, C₁–C₆ alkyl, C₅–C₇ cycloalkyl, C₆–C₁₂ alkylcycloalkyl, halogenated C₁–C₆ alkyl and the other of R³ and R⁴ is C₆–C₁₀ aryl, C₇–C₁₂ alkylaryl, halogenated C₆–C₁₀ aryl, or halogenated C₇–C₁₂ alkylaryl; and one of R⁵ and R⁶ is hydrogen, and the other of R⁵ and R⁶ is C₁–C₆ alkyl, halogenated C₁–C₆ alkyl, or carboxylic acid C₁–C₆ alkyl ester. In one aspect of this embodiment, R³ is hydrogen, C₁–C₆ alkyl, C₅–C₇ cycloalkyl, C₆–C₁₂ alkylcycloalkyl, or halogenated C₁–C₆ alkyl; R⁴ is C₆–C₁₀ aryl, C₇–C₁₂ alkylaryl, halogenated C₆–C₁₀ aryl, or halogenated C₇–C₁₂ alkylaryl; R⁵ is C₁–C₆ alkyl, halogenated C₁–C₆ alkyl, or carboxylic acid C₁–C₆ alkyl ester; and R⁶ is hydrogen. In another aspect of this embodiment, R³ is hydrogen; R⁴ is C₆–C₁₀ aryl, C₇–C₁₂ alkylaryl, halogenated C₆–C₁₀ aryl, or halogenated C₇–C₁₂ alkylaryl; R⁵ is C₁–C₆ alkyl, halogenated C₁–C₆ alkyl, or carboxylic acid C₁–C₆ alkyl ester; and R⁶ is hydrogen.

Exemplary olefin compounds suitable for use in the present invention include, but are not limited to, C₃ to C₃₀ aliphatic hydrocarbon mono-olefins such as propylene, 1-butene, 2-butene, isobutene, 1-pentene, 2-pentene, 2,3-dimethyl-2-butene, and the like; C₄ to C₃₀ aliphatic hydrocarbon diolefins such as 1,3-butadiene, 1,3-pentadiene, 1,4-pentadiene, 1,4-hexadiene, etc.; C₅ to C₁₀ alicyclic hydrocarbon olefins and diolefins such as cyclopentene, cyclopentadiene, cyclohexene, cyclohexadiene, cyclooctene, and cyclooctadiene; unsaturated bicyclics such as norbornene, norbornadiene, 1,4-dihydronaphthalene, and indene; aromatic-containing hydrocarbon olefins such as styrene, α-methylstyrene, α-ethylstyrene, 1-ethenyl-2-methylbenzene, 1-ethenyl-2,6-dimethylbenzene, 1-ethenyl-2,5-dimethylbenzene, 1-phenyl-1-propylethylene, 1-phenyl-1-n-butylethylene, 1-phenyl-1-n-pentylethylene, 1-phenyl-1-n-hexylethylene, 1-phenyl-1-isopropylethylene, 1-phenyl-1-tert-butylethylene, 1-phenyl-1-cyclopropylethylene, 1-phenyl-1-cyclobutylethylene, 1-phenyl-1-cyclopentylethylene, 1-phenyl-1-cyclohexylethylene, trans-1-phenyl-2-methylethylene, cis-1-phenyl-2-methylethylene, 1-phenyl-2,2,-dimethylethylene, 1-methylene-1,2,3,4-tetrahydronaphthalene, 1-methylene-2,2-dimethyl-1,2,3,4-tetrahydronaphthalene; and 1-methylene-2,3-dihydroindene; and halogenated hydrocarbon olefins such as trifluoromethylethylene, perfluoropropylethylene, perfluorooctylethylene, trichloromethylethylene, 3-fluoro-1-propylene, 3-chloro-1-propylene, 3-bromo-1-propylene, 3-iodo-1-propylene, trans-1-(4-fluorophenyl)-1-propylene, trans-1-(2-fluorophenyl)-1-propylene, trans-1-(2,4-difluorophenyl)-1-propylene, and trans-1-(3,4-difluorophenyl)-1-propylene.

Other olefin compounds suitable for use in the present invention include, but are not limited to, acrylic esters such as the alkyl esters of cinnamic acid (methyl cinnamate, ethyl cinnamate, n-propyl cinnamate, isopropyl cinnamate, and so forth), phenyl cinnamate, benzyl cinnamate, the alkyl esters of β-halophenylacrylic acid such as the methyl, ethyl, n-propyl and isopropyl esters of β-(4-fluorophenyl)acrylic acid, β-(2-fluorophenyl)acrylic acid, β-(2,4-difluorophenyl)acrylic acid, and β-(3,4-difluorophenyl)acrylic acid.

The carbamate employed in the process of the invention is a carbamate of Formula (IV):

(IV)

wherein R⁸ is selected from C₁–C₂₀ hydrocarbyl and substituted C₁–C₂₀ hydrocarbyl. In one embodiment of Formula (IV), R⁸ is selected from C₁–C₆ alkyl, substituted C₁–C₆ alkyl, C₇–C₂₀ arylalkyl, and substituted C₇–C₂₀ arylalkyl, wherein the substituents thereon are independently selected from halogen, cyano, nitro, and C₁–C₄ alkoxy. In an aspect of the preceding embodiment, R⁸ is selected from C₁–C₆ alkyl, substituted C₁–C₆ alkyl, C₇–C₁₂ phenylalkyl, and substituted C₇–C₁₂ phenylalkyl, wherein the substituents thereon are independently selected from halogen, cyano, nitro, methoxy, ethoxy, n-propoxy, and isopropoxy. Carbamates suitable for use in the process of the invention include, but are not limited to, methyl carbamate, ethyl carbamate (also referred to in the art as urethane), n-propyl carbamate, t-butyl carbamate, and benzyl carbamate.

The catalyst employed in the process is an osmium catalyst. Suitable osmium catalysts include, but are not limited to, osmium tetroxide, K₂[OsO₂(OH)₄], Na₂[OsO₂(OH)₄], osmium (III) chloride hydrate, and tri-osmium dodecacarbonyl. The osmium catalyst can be, for example, K₂[OsO₂(OH)₄].

The base can be any water-soluble inorganic base. Suitable bases include, but are not limited to, alkali metal hydroxides and alkali metal carbonates, such as NaOH, KOH, CsOH, Na₂CO₃, K₂CO₃, and Cs₂CO₃. A class of the bases within this group is a base selected from NaOH and Cs₂CO₃.

Asymmetric ligands suitable for use in the process of the invention include, but are not limited to, bis(dihydroquinyl)phthalazine ("(DHQ)2PHAL"), bis(dihydroquinidyl)phthalazine ("(DHQD)₂PHAL"), bis(dihydroquinyl)anthraquinone ("(DHQ)₂AQN"), bis(dihydroquinidyl)anthraquinone ("(DHQD)₂AQN"), bis(dihydroquinyl)diphenylphthalazine ("(DHQ)₂DP-PHAL"), bis(dihydroquinidyl)diphenylphthalazine ("(DHQD)₂DP-PHAL"), bis(dihydroquinyl)diphenylpyrazinopyridazine ("(DHQ)₂DPP"), bis(dihydroquinidyl)diphenylpyrazinopyridazine ("(DHQD)₂DPP"), bis(dihydroquinyl)pyrimidine ("(DHQ)₂PYR"), bis(dihydroquinidyl)pyrimidine ("(DHQD)₂PYR"), bis(dihydroquinyl)indoline ("(DHQ)₂IND"), and bis(dihydroquinidyl)indline ("(DHDQ)IND"). A class of the asymmetric ligands within this group is a ligand selected from (DHQ)₂PHAL, (DHQD)₂PHAL, (DHQ)₂AQN, and (DHQD)₂AQN. A sub-class of suitable asymmetric ligands is selected from (DHQ)₂PHAL and (DHQD)₂PHAL. Ligands are commercially available from Aldrich Chemical Company and from ChiRex, Ltd.

The solvent employed in the process of the invention is an aqueous solvent; i.e., the solvent comprises water and optionally a water-soluble organic co-solvent. When the solvent contains an organic co-solvent, water suitably comprises at least about 5 volume percent (e.g., from about 5 to about 95 volume percent), typically comprises at least about 10 volume percent (e.g., from about 10 to about 95 volume percent), and often comprises at least 25 volume percent (e.g., from about 25 to about 95 volume percent) based on the total volume of solvent. In one embodiment, the aqueous solvent comprises from about 30 to about 70 volume percent (e.g., from about 40 to about 60 volume percent, or from about 45 to about 55 volume percent) water, with the balance of the solvent being an organic co-solvent. Suitable co-solvents include, but are not limited to, $C_1$–$C_6$ monohydric alcohols (e.g., methanol, ethanol, n-propanol, n-butanol, n-pentanol, isopropanol, and sec-butyl alcohol), $C_2$–$C_8$ polyhydric alcohols (e.g., ethylene glycol, propylene glycol, and glycerol), $C_1$–$C_4$ nitrites (e.g., acetonitrile and propionitrile), ethers (e.g., tetrahydrofuran, diethyl ether, methyl-tert-butyl ether), dimethylformamide, and dimethylsulfoxide. A class of suitable co-solvents comprises ethanol, n-propanol, isopropanol, and n-butanol; i.e., the aqueous solvent comprises water and a co-solvent selected from ethanol, n-propanol, isopropanol, and n-butanol. A sub-class is n-propanol; i.e., the aqueous solvent comprises water and n-propanol.

The relative proportions of the carbamate and the olefin compound employed in the process of the invention can vary over a wide range, wherein the only requirement is that the proportions of carbamate and olefin employed result in the conversion of at least a portion of the starting olefin compound to β-hydroxy carbamate product. The mole ratio of carbamate to olefin compound employed in the process of the invention is suitably in the range of from about 10:1 to about 1:10, and is typically in the range of from about 5:1 to about 1:5 (e.g., from about 2:1 to about 1:2). A molar excess of carbamate can be employed in order to optimize conversion of the olefin; i.e., the mole ratio of carbamate to olefin is at least about 1.1:1 (e.g., from about 1.1:1 to about 1.5:1).

The amount of base employed in the process is suitably in the range of from about 0.5 to about 3.5 mole equivalents, and is typically from about 1 to about 3.5 mole equivalents (e.g., from about 2.5 to about 3 mole equivalents), per mole equivalent of starting olefin. In one embodiment, the amount of base is in the range of from about 2 to about 3.1 mole equivalents (e.g., about 3 mole equivalents) per mole equivalent of starting olefin.

The amount of the co-oxidant (i.e., hydantoin of Formula (Ia) or isocyanuric acid of Formula (Ib) or its alkali metal salt) employed in the process is suitably in the range of from about 0.5 to about 2 mole equivalents, and is typically from about 1 to about 2 mole equivalents (e.g., from about 1.4 to about 1.6 mole equivalents), per mole equivalent of starting olefin. In one embodiment, the amount of co-oxidant is in the range of from about 1.2 to about 1.8 mole equivalents (e.g., about 1.5 equivalents) per mole equivalent of starting olefin.

The amount of osmium catalyst employed in the process is suitably in the range of from about 0.1 to about 30 mole percent, and is typically in the range of from about 0.5 to about 20 percent (e.g., from about 1 to about 10 mole percent), based upon the total number of moles of osmium and olefin compound employed in the process. In one embodiment, the amount of osmium catalyst is in the range of from about 2 to about 5 mole percent.

The amount of asymmetric ligand employed in the process is suitably in the range of from about 1 to about 3 mole equivalents, and is typically from about 1.1 to about 2 mole equivalents, per mole equivalent of osmium employed in the process. In one embodiment, the amount of asymmetric ligand is in the range of from about 1.1 to about 1.5 mole equivalents.

The process of the invention is suitably conducted at a temperature in the range of from about 0 to about 30° C., and is typically conducted at a temperature in the range of from about 10 to about 30° C. In one embodiment, the temperature is in the range of from about 15 to about 25° C. (e.g., from about 20 to about 25° C.).

The reaction time depends upon such factors as the choice and relative amounts of olefin compound, carbamate, osmium catalyst, co-oxidant, asymmetric ligand, base, and solvent and the reaction temperature, and thus can vary over a wide range. Nonetheless, the reaction time is typically in the range of from about 0.1 to about 24 hours, and is often in the range of from about 0.5 to about 8 hours (e.g., from about 1 to about 4 hours).

The reactants, catalyst, solvent, and other agents can be added to the reaction vessel concurrently. Alternatively, the reactants, solvent, and other agents can be added concurrently or sequentially in any order, followed by addition of the catalyst. The base is typically added in the form of an aqueous solution, and the osmium catalyst is typically added as an aqueous solution formed, e.g., by dissolution of the catalyst in a small portion of the aqueous base. One procedure for introducing the reactants, etc. into the reaction vessel is as follows: (1) the base is dissolved in water, and a small portion of the resulting basic solution is used to dissolve the osmium catalyst; (2) the balance of the basic solution is added to the reaction vessel, followed by addition of a portion of the co-solvent (if any) and the carbamate concurrently or sequentially in either order, and then the co-oxidant; (3) the remaining co-solvent (if any) is then added, followed by the asymmetric ligand and olefin concurrently or sequentially in either order, and then the catalyst.

The progress of the reaction can be followed by monitoring the disappearance of the olefin using TLC, HPLC, or GC.

Conversions of olefin compound to β-hydroxy carbamate of at least about 60% are typically achieved using equimolar or higher amounts of carbamate. Conversions of the starting olefin compound of from about 80% to about 100% (e.g., from about 90% to about 99%) can be achieved.

The β-hydroxy carbamate product can be recovered from the reaction mixture by dilution with water and extraction with an organic solvent, concentration (e.g., by evaporative removal of the solvent), and then crystallization or flash chromatography. Suitable organic solvents include, but are not limited to, ethers (e.g., tetrahydrofuran, diethyl ether, and methyl-tert-butyl ether), aromatic hydrocarbons (e.g., toluene, the xylenes, and ethylbenzene), and allyl acetates (e.g., ethyl acetate and isopropyl acetate). Polar organic solvents (e.g., an ether or an alkyl acetate) are preferred.

The process of the present invention is particularly useful for preparing asymmetric β-hydroxy carbamates from suitable starting olefins (described in the next paragraph), wherein the process involves the asymmetric addition of a carbamoyl group and a hydroxy group to the olefin compound. Enantioselectivity is typically achieved via the process of the invention; i.e., the β-hydroxy carbamate product typically has an enantiomeric excess ("ee") of one of the enantiomers which can be formed by addition of the carbamoyl and hydroxy groups to the carbon-carbon double bond.

An olefin compound suitable for use in preparing asymmetric β-hydroxy carbamates via the process of the invention is characterized by the absence of a $C_2$ axis of symmetry parallel to the double bond. The olefin compound suitably has from 2 to about 40 carbon atoms, typically has from 2 to about 30 carbon atoms (e.g., from 2 to about 24 carbon atoms). A $C_2$ axis of symmetry is defined herein as an axis passing through the molecule wherein after rotation of the molecule by 180 degrees about the axis, the molecule appears exactly the same as it was before the rotation. Olefin compounds which are not capable of asymmetric addition at the double bond include those having one of the following general structures

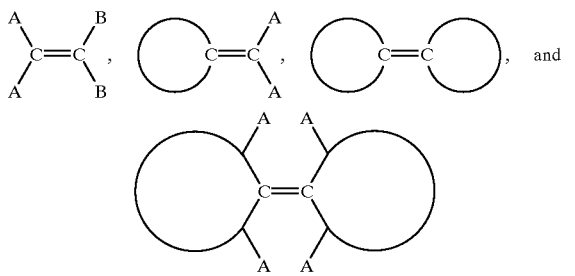

wherein A and B denote organic groups and the broken circles denote symmetrical ring systems; i.e., ring systems which provide a $C_2$ axis of symmetry for the compound parallel to the carbon-carbon double bond.

Generally speaking, olefin compounds suitable for use in preparing the asymmetric β-hydroxy carbamate products via the process of the invention are the olefin compounds as previously defined and described which also do not possess a $C_2$ axis of symmetry parallel to the double bond. Accordingly, in one-embodiment, the olefin compound is a hydrocarbon or a substituted hydrocarbon (as defined above) containing at least one carbon-carbon double bond and characterized by the absence of a $C_2$ axis of symmetry parallel to the double bond. In another embodiment, the olefin compound is an acrylic ester of Formula (II) as described above. In another embodiment, the olefin compound is a mono-substituted olefin, 1,1-disubstituted olefin, cis-disubstituted olefin, trans-disubstituted olefin, tri-substituted olefin, or tetra-substituted olefin, wherein each substituent is selected from hydrocarbyl, substituted hydrocarbyl, carboxylic acid hydrocarbyl ester, and carboxylic acid substituted hydrocarbyl ester; provided that (i) the substituents on the 1,1-disubstituted olefin are not the same and (ii) when the substituents on one carbon of the double bond in the tetra-substituted olefin are the same, the substituents on the other carbon of the double bond are different (i.e., there is no $C_2$ axis of symmetry parallel to the double bond in the 1,1-disubstituted olefin or the tetra-substituted olefin). In one aspect of the preceding embodiment, the olefin compound is selected from the group consisting of mono-substituted, 1,1-disubstituted, trans-disubstituted, and trisubstituted olefins, wherein each substituent is independently $C_1$–$C_{18}$ hydrocarbyl, substituted $C_1$–$C_{18}$ hydrocarbyl, carboxylic acid $C_1$–$C_8$ hydrocarbyl ester, or carboxylic acid substituted $C_1$–$C_8$ hydrocarbyl ester; with the proviso that the substituents on the 1,1-disubstituted olefin are not the same. In another aspect, the olefin compound is selected from the group consisting of mono-substituted, 1,1-disubstituted, trans-disubstituted, and trisubstituted olefins, wherein one substituent is selected from carboxylic acid $C_1$–$C_8$ hydrocarbyl ester and carboxylic acid substituted $C_1$–$C_8$ hydrocarbyl ester, and the remaining substituent on the 1,1- and the trans-disubstituted olefins and the remaining substituents trisubstituted olefin are independently selected from hydrocarbyl and substituted hydrocarbyl (e.g., $C_1$–$C_{18}$ hydrocarbyl and substituted $C_1$–$C_{18}$ hydrocarbyl); with the proviso that the substituents on the 1,1-disubstituted olefin are not the same.

In yet another embodiment, the olefin compound is a compound of formula (III) as defined above, provided that,
(1) when $R^3$, $R^4$, $R^5$ and $R^6$ are separate substituents (i.e., no two of $R^3$, $R^4$, $R^5$ and $R^6$ together form part of a ring system), then (i) $R^5$ is different from $R^6$, when $R^3$ is the same as $R^4$ and (ii) $R^3$ is different from $R^4$, when $R^5$ is the same as $R^6$;
(2) when $R^3$ and $R^4$ together with the carbon atom to which they are attached form a ring system, $R^5$ and $R^6$ are separate substituents, and $R^5$ is the same as $R^6$, then the ring system incorporating $R^3$ and $R^4$ is not symmetrical with respect to a $C_2$ axis of symmetry parallel to the carbon-carbon double bond; or
(3) when $R^3$ and $R^4$ together with the carbon atom to which they are attached form a ring system and $R^5$ and $R^6$ together with the carbon atom to which they are attached form another ring system, the compound so formed is characterized by the absence of a $C_2$ axis of symmetry parallel to the carbon-carbon double bond.

Exemplary olefin compounds suitable for use in the asymmetric aminohydroxylation process of the invention include, but are not limited to, all of the exemplary olefin compounds described earlier, except for 2,3-dimethyl-2-butene, which has a $C_2$ axis of symmetry parallel to the carbon-carbon double bond.

It is understood that, in cases where a starting olefin not capable of conversion to an asymmetric β-hydroxy carbamate product is employed in the process of the invention or in cases where an enantiomeric excess of an asymmetric product is not desired, the presence of an asymmetric ligand is optional. An asymmetric ligand is nonetheless typically employed, because the reaction, whether chiral or achiral, is often accelerated and/or exhibits regioselectivity due to the presence of the ligand.

The process of the invention also includes treating the β-hydroxy carbamate product prepared as described above with additional base to form at least one oxazolidinone. As used herein, the term "treating" and variants thereof (e.g., "treated") mean either the addition of the carbamate product to the base or the addition of the base to the carbamate product. In one embodiment, the β-hydroxy carbamate is recovered from the reaction mixture as described above, and then treated with base. Another embodiment is a "one-pot" procedure, wherein the base is brought directly into contact with the reaction mixture containing the β-hydroxy carbamate product (typically by addition of the base to the reaction mixture), thereby eliminating the β-hydroxy carbamate recovery step. The additional base can be any of the bases disclosed above for use in the process for preparing the β-hydroxy carbamate product. The additional base can be the same or different from the based employed to form the hydroxy carbamate; e.g., NaOH can be used both for forming hydroxy carbamate and oxazolidinone, or NaOH can be use to form hydroxy carbamate and $Cs_2CO_3$ to form oxazolidinone. In the "one-pot" procedure, the additional base can be employed either as a solid or in solution; i.e., dissolved in an aqueous solvent as disclosed above for use in the process for preparing the β-hydroxy carbamate product. In treating a recovered β-hydroxy carbamate, the additional base is typically employed as a solution in an aqueous solvent comprising water and at least one co-solvent. The co-solvent is suitably a $C_1$–$C_6$ monohydric alcohol (e.g., methanol, ethanol, n-propanol, n-butanol, n-pentanol, and so forth). While the β-hydroxy carbamate can be mixed with the basic solution directly, it is more typically employed as a solution in an appropriate solvent, such as an aqueous solvent comprising water and a $C_1$–$C_6$ monohydric alcohol co-solvent.

In the one-pot procedure, the amount of additional base employed is suitably in the range of from about 0.5 to about 20 mole equivalents, and is typically in the range of from about 1 to about 5 mole equivalents (e.g., from about 2 to about 4 mole equivalents), per mole equivalent of starting olefin. In treating a recovered hydroxy carbamate product with additional base, the amount of base employed is suitably in the range of from about 0.5 to about 20 mole equivalents, and is typically in the range of from about 1 to about 5 mole equivalents (e.g., from about 2 to about 4 mole equivalents), per mole equivalent of hydroxy carbamate.

The process of treating the β-hydroxy carbamate is suitably conducted at a temperature in the range of from about 0 to about 50° C., and is typically conducted at a temperature in the range of from about 10 to about 30° C. (e.g., from about 15 to about 25° C.).

The reaction time depends upon such factors as the identity and concentration of the β-hydroxy carbamate, the choice and concentration of base, and the reaction temperature, and thus can vary over a wide range. Nonetheless, the reaction time is typically in the range of from about 2 to about 14 hours, and is often in the range of from about 1 to about 6 hours.

The progress of the reaction can be followed by monitoring the disappearance of hydroxy carbamate or the formation of oxazolidinone product using GC, HPLC, TLC, or NMR.

Conversions of β-hydroxy carbamate to oxazolidinone of at least about 50% are typically achieved. Conversions of starting hydroxy carbamate to oxazolidinone of from about 80% to about 100% (e.g., from about 90% to about 99%) can be achieved.

The oxazolidinone product can be recovered from the reaction mixture by dilution of the reaction mixture with water, then extraction with a suitable amount, typically 2×1 volume, of an organic solvent, concentration of the extract (e.g., by evaporative removal of the solvent), and then crystallization or flash chromatography. Suitable organic solvents include, but are not limited to, ethers (e.g., tetrahydrofuran, diethyl ether, and methyl-tert-butyl ether), aromatic hydrocarbons (e.g., toluene, the xylenes, and ethylbenzene), and alkyl acetates (e.g., ethyl acetate and isopropyl acetate).

The present invention also includes a process for preparing an oxazolidinone of Formula (V):

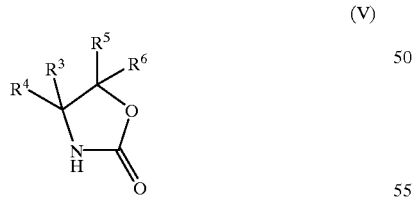

(V)

which comprises:

(A) reacting an olefin compound of formula (III):

(III)

with a carbamate of Formula (IV):

(IV)

in aqueous solvent in the presence of a base, an osmium catalyst, a co-oxidant, and optionally an asymmetric ligand, to form a reaction mixture containing a β-hydroxy carbamate product; and (B) contacting the reaction mixture with additional base to form the oxazolidinone; wherein the co-oxidant employed in (A) is (1) a hydantoin is of Formula (Ia):

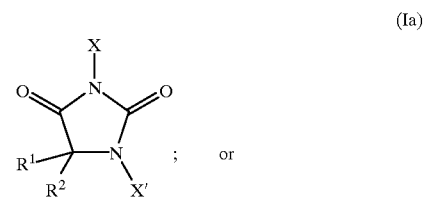

(Ia)

(2) an isocyanuric acid of Formula (Ib):

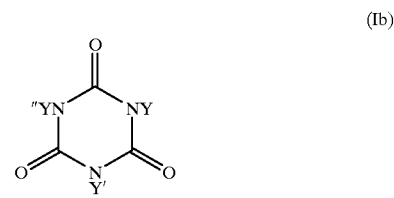

(Ib)

or an alkali metal salt thereof; the olefin compound of Formula (III), the carbamate of formula (IV), and the hydantoin of Formula (Ia), the isocyanuric acid of Formula (Ib), and the asymmetric ligand are as heretofore defined; and $R^3$, $R^4$, $R^5$ and $R^6$ in the oxazolidinone of Formula (V) have the same meaning as in the olefin compound of Formula (III), except that in Formula (V) when $R^3$ and $R^5$ together with the carbon atoms to which they are attached form a 5- to 10-membered monocyclic or bicyclic carbocyclic ring system, the ring system may be saturated or unsaturated.

The present invention also includes a process for preparing an asymmetric oxazolidinone of Formula (V-1):

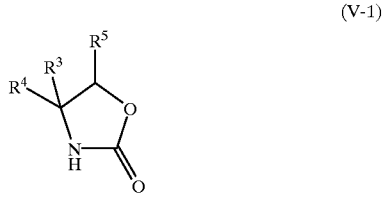

(V-1)

which comprises:

(A-1) reacting an olefin compound of formula (VI):

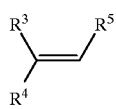
(VI)

with a carbamate of Formula (IV):

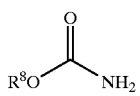
(IV)

in aqueous solvent in the presence of a base, an osmium catalyst, an asymmetric ligand, and a co-oxidant to form a reaction mixture containing an asymmetric β-hydroxy carbamate product; and (B-1) contacting the reaction mixture with additional base to form the oxazolidinone;

wherein the co-oxidant employed in (A) is
(1) a hydantoin is of Formula (Ia):

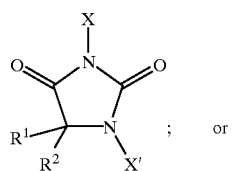
(Ia)

; or (2) an isocyanuric acid of Formula (Ib):

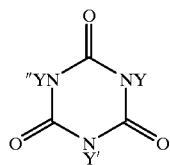
(Ib)

or an alkali metal salt thereof; and wherein $R^3$ and $R^4$ are each independently selected from hydrogen, $C_1$–$C_{12}$ alkyl, $C_2$–$C_{12}$ alkenyl, $C_3$–$C_8$ cycloalkyl, $C_4$–$C_{20}$ alkylcycloalkyl, $C_4$–$C_{20}$ cycloalkyl-alkyl, $C_5$–$C_8$ cycloalkenyl, $C_6$–$C_{20}$ alkylcycloalkenyl, $C_6$–$C_{20}$ cycloalkenylalyl, $C_6$–$C_{10}$ aryl, $C_7$–$C_{20}$ alkylaryl, $C_8$–$C_{20}$ alkenylaryl, $C_7$–$C_{20}$ arylalkyl, heterocyclic, carboxylic acid $C_1$–$C_8$ alkyl ester, substituted $C_1$–$C_{12}$ alkyl, substituted $C_2$–$C_{12}$ alkenyl, substituted $C_3$–$C_8$ cycloalkyl, substituted $C_4$–$C_{20}$ alkylcycloalkyl, substituted $C_4$–$C_{20}$ cycloalkyl-alkyl, substituted $C_5$–$C_8$ cycloalkenyl, substituted $C_6$–$C_{20}$ alkylcycloalkenyl, substituted $C_6$–$C_{20}$ cycloalkenylalkyl, substituted $C_6$–$C_{10}$ aryl, substituted $C_7$–$C_{20}$ alkylaryl, substituted $C_8$–$C_{20}$ alkenylaryl, substituted $C_7$–$C_{20}$ arylalkyl, substituted heterocyclic, and carboxylic acid substituted $C_1$–$C_8$ alkyl ester, wherein the substituents thereon are independently selected from halogen, hydroxy, $(CH_2)_{0-2}OR^7$, nitro, cyano, $(CH_2)_{0-2}COOR^7$, $COR^7$, $(CH_2)_{0-2}CON(R^7)_2$, and $N(R^7)_2$; or $R^3$ and $R^4$ together with the carbon atom to which they are attached form a 5- to 10-membered monocyclic or bicyclic saturated or unsaturated carbocyclic ring system which is optionally substituted with one or more of $C_1$–$C_8$ alkyl, halogen, hydroxy, and $(CH_2)_{0-2}OR^7$;

$R^5$ is selected from hydrogen, $C_1$–$C_{12}$ alkyl, $C_2$–$C_{12}$ alkenyl, $C_3$–$C_8$ cycloalkyl, $C_4$–$C_{20}$ alkylcycloalkyl, $C_4$–$C_{20}$ cycloalkyl-alkyl, $C_5$–$C_8$ cycloalkenyl, $C_6$–$C_{20}$ alkylcycloalkenyl, $C_6$–$C_{20}$ cycloalkenylalyl, $C_6$–$C_{10}$ aryl, $C_7$–$C_{20}$ alkylaryl, $C_8$–$C_{20}$ alkenylaryl, $C_7$–$C_{20}$ arylalkyl, heterocyclic, carboxylic acid $C_1$–$C_8$ alkyl ester, substituted $C_1$–$C_{12}$ alkyl, substituted $C_2$–$C_{12}$ alkenyl, substituted $C_3$–$C_8$ cycloalkyl, substituted $C_4$–$C_{20}$ alkylcycloalkyl, substituted $C_4$–$C_{20}$ cycloalkyl-alkyl, substituted $C_5$–$C_8$ cycloalkenyl, substituted $C_6$–$C_{20}$ alkylcycloalkenyl, substituted $C_6$–$C_{20}$ cycloalkenylalkyl, substituted $C_6$–$C_{10}$ aryl, substituted $C_7$–$C_{20}$ alkylaryl, substituted $C_8$–$C_{20}$ alkenylaryl, substituted $C_7$–$C_{20}$ arylalkyl, substituted heterocyclic, and carboxylic acid substituted $C_1$–$C_8$ alkyl ester, wherein the substituents thereon are independently selected from halogen, hydroxy, $(CH_2)_{0-2}OR^7$, nitro, cyano, $(CH_2)_{0-2}COOR^7$, $COR^7$, $(CH_2)_{0-2}CON(R^7)_2$, and $N(R^7)_2$;

provided that (i) at least one of $R^3$, $R^4$, and $R^5$ is not hydrogen; (ii) when $R^3$ is the same as $R^4$, $R^5$ is not hydrogen; and (iii) when $R^3$ and $R^4$ together with the carbon atom to which they are attached form a carbocyclic ring system which is symmetrical with respect to a $C_2$ axis bisecting the ring and also passing through the carbon atom in the oxazolidinone ring to which $R^3$ and $R^4$ are attached, $R^5$ is not hydrogen;

$R^7$ is $C_1$–$C_6$ alkyl; and the carbamate of Formula (IV), the hydantoin of Formula (Ia), and the isocyanuric acid of Formula (Ib) are as heretofore defined.

Depending upon the groups selected for $R^3$, $R^4$, and $R^5$ respectively, the carbon atom in the oxazolidinone ring to which $R^5$ is attached can be the chiral center, or the carbon atom in the oxazolidinone ring to which $R^3$ and $R^4$ are attached can be the chiral center, or both of the foregoing ring carbons can be chiral centers. When the oxazolidinone of Formula (V-1) has one chiral center, the reaction product normally has an enantiomeric excess of one of the two possible enantiomers. When the oxazolidinone of Formula (V-1) has two chiral centers, the reaction product normally has an excess of one of the four possible isomers.

In one aspect of the process for preparing an oxazolidinone of Formula (V-1), $R^3$ is hydrogen; and all other variables and provisos are as defined and set forth above.

In another aspect of the process for preparing an oxazolidinone of Formula (V-1), one of $R^3$ and $R^4$ is hydrogen, $C_1$–$C_6$ alkyl, $C_5$–$C_7$ cycloalkyl, $C_6$–$C_{14}$ alkylcycloalkyl, halogenated $C_1$–$C_6$ alkyl and the other of $R^3$ and $R^4$ is $C_6$–$C_{10}$ aryl, $C_7$–$C_{12}$ alkylaryl, halogenated $C_6$–$C_{10}$ aryl, or halogenated $C_7$–$C_{12}$ alkylaryl; and $R^5$ is hydrogen, $C_1$–$C_6$ alkyl, substituted $C_1$–$C_6$ alkyl, and carboxylic acid $C_1$–$C_6$ alkyl ester wherein the substituents on the alkyl are independently selected from halogen, hydroxy, and $(CH_2)_{0-2}OR^7$; and all other variables are as defined above.

In yet another aspect of the process for preparing an oxazolidinone of Formula (V-1), $R^3$ is hydrogen, and $R^4$ is $C_6$–$C_{10}$ aryl, $C_7$–$C_{12}$ alkylaryl, halogenated $C_6$–$C_{10}$ aryl, or halogenated $C_7$–$C_{12}$ alkylaryl; and $R^5$ is hydrogen, $C_1$–$C_6$ alkyl, substituted $C_1$–$C_6$ alkyl, and carboxylic acid $C_1$–$C_6$ alkyl ester wherein the substituents on the alkyl are independently selected from halogen, hydroxy, and $(CH_2)_{0-2}OR^7$; and all other variables are as defined above.

In still another aspect of the process for preparing an oxazolidinone of Formula (V-1), $R^3$ is hydrogen; $R^4$ is a group of Formula (VII):

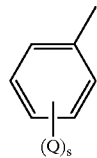
(VII)

wherein each Q is independently selected from halogen, hydroxy, $C_1-C_6$ alkyl, halogenated $C_1-C_6$ alkyl, $(CH_2)_{0-2}OR^7$, nitro, cyano, $(CH_2)_{0-2}COOR^7$, $COR^7$, $(CH_2)_{0-2}CON(R^7)_2$, and $N(R^7)_2$;

$R^5$ is selected from hydrogen, $C_1-C_6$ alkyl, substituted $C_1-C_6$ alkyl, and carboxylic acid $C_1-C_6$ alkyl ester; wherein the substituents on the alkyl are independently selected from halogen, hydroxy, and $(CH_2)_{0-2}OR^7$;

s in an integer from 0 to 5, or from 1 to 3, or is 1 or 2; and all other variables are as defined above.

In still another aspect of the process for preparing an oxazolidinone of Formula (V-1), $R^4$ is a group of Formula (VII), wherein Q is fluorine; and all other variables are as heretofore defined.

In still another aspect of the process for preparing-an oxazolidinone of Formula (V-1), the oxazolidinone is of formula (V-1a):

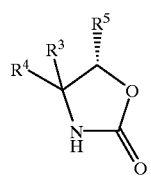
(V-1a)

wherein $R^3$, $R^4$, and $R^5$ are as defined above.

In still another aspect of the process for preparing an oxazolidinone of Formula (V-1), the oxazolidinone is of formula (V-1b):

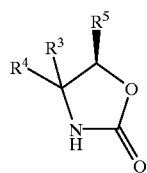
(V-1b)

wherein $R^3$, $R^4$, and $R^5$ are as defined above.

In still another aspect of the process for preparing an oxazolidinone of Formula (V-1), the oxazolidinone is of formula (V-1c):

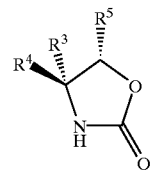
(V-1c)

or of formula (V-1d):

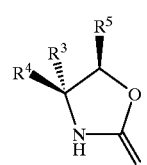
(V-1d)

wherein $R^3$ is hydrogen; $R^4$ is $C_6-C_{10}$ aryl, $C_7-C_{12}$ alkylaryl, halogenated $C_6-C_{10}$ aryl, or halogenated $C_7-C_{12}$ alkylaryl; and $R^5$ is hydrogen, $C_1-C_6$ alkyl, substituted $C_1-C_6$ alkyl, and carboxylic acid $C_1-C_6$ alkyl ester, wherein the substituents on the alkyl are independently selected from halogen, hydroxy, and $(CH_2)_{0-2}OR^7$; and all other variables are as defined above. In an illustration of this aspect, $R^4$ is a group of Formula (VII) as defined above; e.g., 2-fluorophenyl, 3,4-difluorophenyl, or 4-fluorophenyl.

The co-oxidant, the carbamate of Formula (IV), the aqueous solvent, base, osmium catalyst, and asymmetric ligand employed in the process for preparing an oxazolidinone of Formula (V) or (V-1) are the same as earlier defined and described. In particular, the relative proportions of reactants and reagents and the reaction conditions employed in this process are the same as earlier defined and described.

The procedures available for recovering the oxazolidinone of Formula (V) or (V-1) from the reaction mixture formed in step (B) or (B-1) depend in part on the nature of the reaction mixture resulting from step (A) or (A-1). In step (A) or (A-1), the carbamate of Formula (IV) can add to either carbon atom of the carbon-carbon double bond in the olefin of Formula (III) or (VI) and thus can lead to the formation of two β-hydroxy carbamates of Formulas (VIII) and (IX) or (VIII-1) and (IX-1):

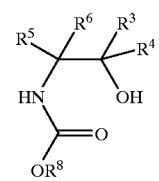
(VIII)

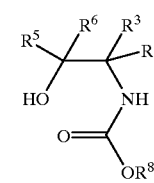
(IX)

-continued

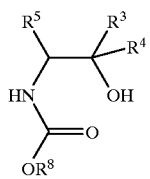
(VIII-1)

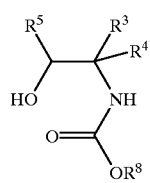
(IX-1)

The subsequent contact of any of a variety of bases (e.g., alkali metal hydroxides including NaOH and KOH) with the mixture of step (A) or (A-1) containing the β-hydroxy carbamates leads to ring closure and the formation of a mixture including the oxazolidinone of Formula (V) or (V-1) and an oxazolidinone of Formula (X) or (X-1):

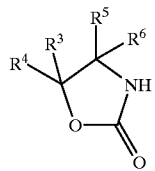
(X)

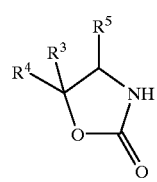
(X-1)

Separation of the mixture of oxazolidinone products can be carried out using known techniques such as chromatography, crystallization, and solvent extraction.

It has been discovered that, when the mixture of step (A) or (A-1) containing the β-hydroxy carbamates is brought into contact with an alkali metal carbonate, and then acidified (e.g., by adding and refluxing with a strong acid such as hydrochloric acid, nitric acid, or sulfuric acid), only the oxazolidinone of Formula (V) or (V-1) is formed; i.e., the mixture resulting from step (B) or (B-1) includes the oxazolidinone of Formula (V) or (V-1) and a hydroxyamine of Formula (XI) or (XI-1):

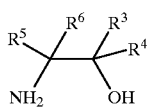
(XI)

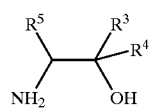
(XI-1)

The oxazolidinone of Formula (X) or (X-1) is not formed. A class of the group of suitable alkali metal carbonates is potassium carbonate and cesium carbonate. A sub-class is cesium carbonate. Separation and recovery of the oxazolidinone of Formula (V) or (V-1) from the hydroxyamine of Formula (XI) or (XI-1) can be achieved via neutralization of the acidified mixture with a base such as those heretofore described (e.g., NaOH), and extraction with an organic solvent such as those heretofore described (e.g., MTBE, ethyl acetate, or isopropyl acetate).

The yield of oxazolidinone of Formula (V) or (V-1) depends upon the choice and amounts of starting olefin compound of Formula (III) or (VI), starting carbamate of Formula (IV), co-oxidant, catalyst, and solvent, and on the reaction conditions employed. Nonetheless, the yield is typically at least about 20%, and is often at least about 50%, based on the starting olefin compound.

The present invention further includes a process for reacting an amine with any of the oxazolidinones described above to obtain a coupled amine product. More particularly, the process comprises treating the oxazolidinone with a deprotonation agent; then contacting the treated oxazolidinone with a formulating agent to provide a formulated intermediate; and then contacting the formulated intermediate with a primary or secondary amine. In one embodiment of the process, the oxazolidinone is an oxazolidinone of Formula (V). Aspects of this embodiment include, but are not limited to, oxazolidinones of Formula (V-1) and of Formula (V-1a), (V-1b), (V-1c), and (V-1d) respectively. In another embodiment, the amine is a hydrocarbyl amine or a substituted hydrocarbyl amine. In still another embodiment, the amine is a primary amine. In still another embodiment, the amine is $C_1$–$C_{12}$ alkylamine, $C_2$–$C_{12}$ alkenylamine, $C_3$–$C_8$ cycloalkylamine, $C_4$–$C_{20}$ alkylcycloalkylamine, $C_4$–$C_{20}$ cycloalkyl-alkylamine, $C_5$–$C_8$ cycloalkenylamine, $C_6$–$C_{20}$ alkylcycloalkenylamine, $C_6$–$C_{20}$ cycloalkenylalkylamine, $C_6$–$C_{10}$ arylamine, $C_7$–$C_{20}$ alkylarylamine, $C_8$–$C_{20}$ alkenylarylamine, $C_7$–$C_{20}$ arylalkylamine, or heterocyclic amine. In still another embodiment, the amine is an amine of Formula (XII):

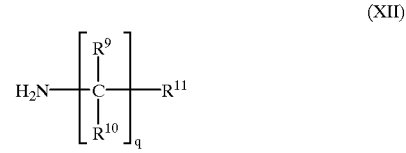
(XII)

wherein $R^9$ and $R^{10}$ are each independently hydrogen, $C_1$–$C_4$ alkyl, or $C_1$–$C_7$ cycloalkyl;

$R^{11}$ is

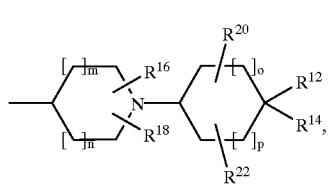
(XIII)

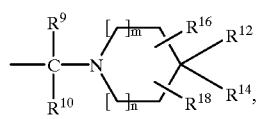
(XIV)

-continued

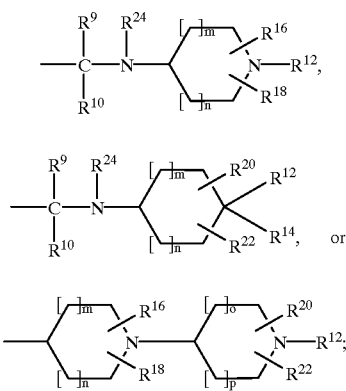

(XV)

(XVI)

(XVII)

wherein $R^{12}$ is selected from phenyl, substituted phenyl, naphthyl, substituted naphthyl, heterocyclic, or substituted heterocyclic; wherein the substituents on the substituted phenyl or naphthyl are independently selected from halogen, hydroxy, trifluoromethyl, cyano, nitro, $C_1$–$C_4$ alkyl, $C_1$–$C_4$ alkoxy, $NHR^a$, and $N(R^a)_2$; the heterocyclic is pyridyl, pyridyl N-oxide (N→O), pyrazinyl, thienyl, thiazolyl, furanyl, or quinazolinyl; and the substituents on the heterocyclic are independently selected from halogen, trifluoromethyl, cyano, nitro, $C_1$–$C_4$ alkyl, $C_1$–$C_4$ alkoxy, phenyl, $C_3$–$C_4$ cycloalkyl, $NHR^a$, and $N(R^a)_2$;

$R^{14}$ is hydrogen, cyano, $C_1$–$C_4$ alkyl, $OR^b$, $CO_2R^b$, CON$(R^a)_2$, phenyl, substituted phenyl, naphthyl, substituted naphthyl, pyridyl, thienyl, furanyl, substituted pyridyl, substituted thienyl, or substituted furanyl; wherein the substituents on the substituted phenyl or naphthyl are independently selected from halogen, trifluoromethyl, cyano, nitro, $C_1$–$C_4$ alkyl, $C_1$–$C_4$ alkoxy, $NHR^a$, and $N(R^a)_2$; and the substituents on the substituted pyridyl, thienyl, or furanyl are independently selected from trifluoromethyl, phenyl, halogen, $C_1$–$C_4$ alkyl, $C_1$–$C_4$ alkoxy, and $C_3$–$C_8$ cycloalkyl;

$R^{16}$, $R^{18}$, $R^{20}$ and $R^{22}$ are each independently selected from hydrogen, $C_1$–$C_{10}$ alkyl, $C_3$–$C_8$ cycloalkyl, $(CH_2)_{0-4}OR^a$, $(CH_2)_{0-4}CF_3$, $(CH_2)_{0-4}CO_2Ra$, $(CH_2)_{0-4}CN$, $(CH_2)_{0-4}NHR^a$, and $(CH_2)_{0-4}N(R^a)_2$;

$R^{24}$ is hydrogen, $C_1$–$C_4$ alkyl, or $C_5$–$C_7$ cycloalkyl;

$R^a$ is $C_1$–$C_4$ alkyl;

$R^b$ is hydrogen, $C_1$–$C_4$ alkyl, $C_3$–$C_8$ cycloalkyl, or $(CH_2)_{1-4}CF_3$;

m, n, o, and p are each independently selected from 0, 1, and 2, with the proviso that the sum of m+n and the sum of o+p are independently never greater than 3; and q is an integer from 0 to 4.

Aspects of the preceding embodiment include, but are not limited to:

$R^9$ and $R^{10}$ are each independently hydrogen or $C_1$–$C_4$ alkyl; or are both hydrogen.

$R^{11}$ is the structure of Formula (XIII) or the structure of Formula (XIV); or is the structure of Formula (XIV).

In $R^{11}$, $R^{12}$ is phenyl, substituted phenyl, pyridyl, or substituted pyridyl; wherein the substituents on the substituted phenyl are independently selected from halogen, trifluoromethyl, cyano, nitro, $C_1$–$C_4$ alkyl, and $C_1$–$C_4$ alkoxy; and the substituents on the substituted pyridyl are independently selected from halogen, trifluoromethyl, cyano, nitro, $C_1$–$C_4$ alkyl, and $C_1$–$C_4$ alkoxy. In another aspect, $R^{12}$ is substituted phenyl wherein the substituents are independently selected from fluorine, cyano, $C_1$–$C_4$ alkyl, and trifluoromethyl, wherein the number of substituents on the phenyl is from 1 to 3 (e.g., from 1 to 2.).

$R^{14}$ is hydrogen, cyano, $C_{1-4}$ alkyl, $OR^b$, phenyl, substituted phenyl, pyridyl, or substituted pyridyl; wherein the substituents on the substituted phenyl are independently selected from halogen, trifluoromethyl, cyano, nitro, $C_{1-4}$ alkyl, and $C_{1-4}$ alkoxy; and wherein the substituents on the substituted pyridyl are independently selected from trifluoromethyl, phenyl, halogen, $C_{1-4}$ alkyl, and $C_{1-4}$ alkoxy. In another aspect, $R^{14}$ is hydrogen, cyano, $C_{14}$ alkyl, or $OR^b$.

$R^{16}$, $R^{18}$, $R^{20}$ and $R^{22}$ are each independently selected from hydrogen, $C_1$–$C_4$ alkyl, $(CH_2)_{0-4}OR^a$, $(CH_2)_{0-4}CF_3$, $(CH_2)_{0-4}CO_2R^a$, and $(CH_2)_{0-4}CN$; or from hydrogen and $C_{1-4}$ alkyl. In another aspect, $R^{16}$, $R^{18}$, $R^{20}$ and $R^{22}$ are all hydrogen.

$R^{24}$ is hydrogen or $C_1$–$C_4$ alkyl; or is hydrogen.

$R^a$ is methyl or ethyl.

$R^b$ is hydrogen or $C_1$–$C_4$ alkyl; or is hydrogen, methyl, or ethyl.

q is 2 or 3.

The coupled amine products are characterized by coupling of the amine to the nitrogen atom in the oxazolidinone ring via a urea linkage. Exemplary of the coupled amine products are products of Formula (XVIII):

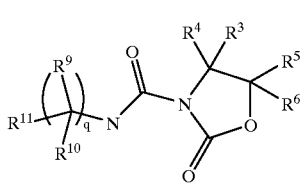

(XVIII)

which results from the coupling of the amine of Formula (XII) and the oxazolidinone of Formula (V). The amines of Formula (XII) can be prepared by procedures described in International Publication No. WO 96/14846, published May 23, 1996 (see, for example, Schemes 1, 6, and 20 therein) and by procedures described in WO 98/57632, WO 98/57638, WO 98/57639, WO 98/57640, WO 98/57641, and WO 98/57642Y, all published on Dec. 23, 1998.

The coupled amine products or salts thereof are useful as intermediates in the formation of, or are useful per se as, pharmaceutically active substances. More particularly, the coupled amine products obtained from oxazolidinones heretofore described and primary amines represented by Formula (XII) are alpha 1a adrenergic receptor antagonists which can be used in the treatment of, for example, benign prostatic hyperplasia.

In the process for reacting an amine with an oxazolidinone to obtain a coupled amine product, the deprotonation agent is an organic or inorganic compound which is sufficiently basic to accept and bind a proton under the reaction conditions. In one embodiment, the deprotonation agent is selected from the group consisting of alkali metal carbonates and bicarbonates, alkali metal salts of di-$C_{1-4}$ alkylamines, alkali metal salts of $C_{1-6}$ hydrocarbons (i.e., methane, ethane, and the linear and branched propanes, butanes, pentanes and hexanes), and alkali metal salts of bis(tri-$C_{1-4}$alkylsilyl)amines. Suitable deprotonation agents include, but are not limited to, lithium diisopropylamide ("LDA"), lithium bis(trimethylsilyl)amide, and butyllithium.

The deprotonation step is typically conducted by treating the oxazolidinone dissolved or suspended in an inert solvent (e.g., aromatic hydrocarbons such toluene, xylene, and ethylbenzene; alkyl ethers such as ethyl ether or THF; aliphatic hydrocarbons such as pentane, hexane, or heptane; and mixtures thereof) with the deprotonation agent (e.g., LDA as either a solid or dissolved or suspended in an aliphatic hydrocarbon, an aromatic hydrocarbon, and/or an ether) for a suitable time and at a suitable temperature for the deprotonation of the oxazolidinone. The order of addition is not important here; i.e., the term "treating" here involves either adding the deprotonation agent to the oxazolidinone or vice versa. The temperature is suitably in the range of from about −80 to about 25° C., and typically in the range of from about −70 to about −25 ° C. (e.g., from about −70 to about −40° C.). While the reaction time (i.e., treating time) can vary widely depending upon the choice of reaction temperature, deprotonation agent, and the particular oxazolidinone reactant employed, it is typically in the range of from about 5 minutes to about 5 hours (e.g., from about 15 minutes to about 2 hours).

Following deprotonation, the deprotonation reaction mixture is contacted with a formylating agent. Suitable formylating agents include, but are not limited to, CDI, phosgene, triphosgene, and chloroformates (e.g., p-nitrophenyl chloroformate, phenylchloroformate, or ethylchloroformate). The term "contacting" here means that the formylating agent (e.g., CDI or p-nitrophenylchloroformate) is added to the reaction mixture or the reaction mixture is added to the formylating agent. It is more typical to add the formylating agent to the reaction mixture. When CDI is employed as the agent, it is typically employed as a solid, although a solution or suspension of CDI in an inert solvent such as THF, toluene, or heptane may be used instead. The mixture resulting from contact with the formylating agent is allowed to react at a temperature suitably in the range of from about −80 to about 40° C., and typically in the range of from about −70 to about 30° C. (e.g. from about −65 to about 25° C.) for a time sufficient to form the formulated intermediate (e.g., acyl imidazolide from CDI). The reaction time is suitably in the range of from about 30 minutes to about 5 hours, and typically in the range of from about 30 minutes to about 3 hours (e.g., from about 45 minutes to about 2 hours). The formation of the intermediate can be monitored by HPLC, and the reaction is typically carried out until at least a major portion of the starting oxazolidinone has been converted to intermediate. The degree of conversion of oxazolidinone to formulated intermediate is typically at least about 60%.

The formulated intermediate is subsequently contacted with a primary or secondary amine, either by addition of the amine to the reaction mixture or vice versa, to form coupled oxazolidinone-amine product. It is more typical to add the amine to the reaction mixture. An amine salt of an organic (e.g., aliphatic carboxylic acids such as acetic acid) or inorganic acid (e.g., HCl or HBr) may optionally be used in place of the amine itself. The amine is typically dissolved or suspended in an inert solvent (e.g., aliphatic hydrocarbons such as pentane, hexane, and/or heptane; ethers such as alkyl ethers—ethyl ether—and/or THF, alkyl acetates such as isopropyl acetate). The coupling of the amine to the oxazolidinone is typically conducted at a temperature in the range of from about −80 to about 40° C. (e.g., from about −70 to about 30° C.). In one embodiment, the reaction mixture is at a relatively low temperature during the addition of the amine (e.g., from about −80 to about −20° C.) and, upon completion of amine addition, is then increased to a relatively high temperature (e.g., from about 0 to about 25° C. ). The coupling can be monitored by HPLC analysis and is typically conducted until at least a major portion of the intermediate has been converted to the coupled amine product. The degree of conversion to coupled product is typically at least about 70%.

After the coupling reaction is complete, the reaction is quenched, typically by the addition of water. The coupled amine product can be recovered via conventional separation techniques such as extraction, chromatography, and crystallization.

In the deprotonation step, the deprotonation agent is suitably employed in an amount of from about 0.8 to about 2.0 mole equivalents, typically in an amount of from about 1.0 to about 1.5 mole equivalents, and preferably in an amount of from about 1.0 to about 1.3 mole equivalents, per mole equivalent of oxazoldinone.

In the formylation step, the formylating agent is employed in an amount of at least about 1 mole equivalent, and is suitably in the range of from about 1.0 to about 1.5 mole equivalents (e.g., from about 1.1 to about 1.3 mole equivalents), per mole equivalent of oxazolidinone.

In the coupling step, the amine is suitably employed in an amount of from about 1.0 to about 2.5 mole equivalents, and typically in an amount of from about 1.1 to about 2.0 mole equivalents (e.g., from about 1.1 to about 1.5 mole equivalents), per mole equivalent of oxazolidinone.

Conversions of at least about 50% (e.g., from about 80% to about 99%) of the starting oxazolidinone to coupled amine product.

The term "substituted" includes multiple degrees of substitution by a named substituent.

A "$C_1$–$C_6$ monohydric alcohol" means a $C_1$–$C_6$ alkyl monoalcohol selected from alcohols of all of the hexyl isomers, alcohols of all of the pentyl isomers, n-, sec-, iso-, and tert-butyl alcohol, n- and iso-propanol, ethanol, and methanol.

A "$C_2$–$C_8$ polyhydric alcohol" means a $C_2$–$C_8$ saturated aliphatic polyalcohol (i.e., diol, triol, tetraol, etc.). Representative examples include ethylene glycol, 1,2- and 1,3-propylene glycol, glycerol, 1,6-hexanediol, pinacol, pentaerythritol and erythritol.

"Hydrocarbyl" means a radical having a carbon atom directly attached to the remainder of the molecule and consisting of one or more carbon atoms and hydrogen atoms. Hydrocarbyl radicals include aliphatic hydrocarbyl groups (e.g., alkyl, alkenyl, or alkynyl), alicyclic hydrocarbyl (e.g., cycloalkyl or cycloalkenyl), aliphatic hydrocarbyl substituted alicyclic hydrocarbyl (e.g., alkyl-substituted cycloalkyl or alkenyl-substituted cycloalkyl), alicyclic hydrocarbyl substituted aliphatic hydrocarbyl (e.g., cycloalkyl-substituted alkyl or cycloalkyl-substituted alkenyl), aromatic hydrocarbyl (e.g., phenyl or naphthyl), aliphatic- and alicyclic-substituted aromatic, aromatic-substituted aliphatic or alicyclic, and the like. The hydrocarbyl radical suitably contains from 1 to about 36 carbon atoms, and typically contains from 1 to about 20 carbon atoms (e.g., from 1 to about 12 carbon atoms, or from 1 to about 8 carbon atoms).

"Substituted hydrocarbyl" means a radical having a carbon atom directly attached to the remainder of the molecule and consisting of one or more carbon atoms and hydrogen atoms, wherein (i) one or more of the hydrogen atoms have been replaced by one or more heteroatom-containing substituents such as halogen, hydroxy (—OH), mercapto (—SH), oxo (═O), alkoxy (—O-alkyl), primary amino (—NH$_2$), N-alkylamino (—NH-alkyl), N,N-dialkylamino (—N(alkyl)$_2$), carboxamido (—C(═O)NH$_2$), carboxy (—COOH), alkoxycarbonyl (—C(═O)O-alkyl), alkylcarbonyl (C(=O)-alkyl), formyl (—CHO), nitro (—NO$_2$), cyano (—CN), and the like, wherein alkyl means a linear or branched alkyl group, (ii) from one to no more than half (i.e., from one to no more than 1 in 2, and typically to no more than 1 in 3; e.g., no more than 1 in 4 or no more than 1 in 5) of the carbon atoms have been replaced by one or more heteroatoms independently selected from nitrogen, oxygen, sulfur, silicon, and phosphorus (and is typically independently selected from nitrogen, oxygen, and sulfur), or (iii) a combination of carbon atoms and hydrogen atoms have been replaced in accordance with (i) and (ii). The substituted hydrocarbyl radical suitably contains from 1 to about 36 carbon atoms, and typically contains from 1 to about 20 carbon atoms (e.g., from 1 to about 12 carbon atoms, or from 1 to about 8 carbon atoms).

"$C_1$–$C_4$ alkoxy" means an alkoxy group selected from methoxy, ethoxy, n-propoxy, isopropoxy, n-butoxy, isobutoxy, tert-butoxy, and sec-butoxy.

As used herein, the term "$C_1$–$C_{12}$ alkyl" refers to a $C_1$ to $C_{12}$ linear or branched alkyl group; i.e., the term includes all of the dodecyl, undecyl, decyl, nonyl, octyl, heptyl, hexyl, and pentyl isomers as well as n-, iso-, sec- and t-butyl, n- or isopropyl, ethyl and methyl. Similarly, "$C_1$–$C_8$ alkyl" refers to a $C_1$ to $C_8$ linear or branched alkyl group; i.e., all of the octyl, heptyl, hexyl and pentyl isomers, whether linear or branched, n-, iso-, sec- and t-butyl, n- or isopropyl, ethyl and methyl. "$C_1$–$C_6$ alkyl" refers to a $C_1$ to $C_6$ linear or branched alkyl group; i.e., all of the hexyl and pentyl isomers, whether linear or branched, n-, iso-, sec- and t-butyl, n- or isopropyl, ethyl and methyl. "$C_1$–$C_4$ alkyl" means a $C_1$ to $C_4$ linear or branched alkyl group and refers to n-, iso-, sec- and t-butyl, n- or isopropyl, ethyl and methyl.

"$C_2$–$C_{12}$ alkenyl" refers to a $C_2$ to $C_{12}$ linear or branched alkenyl group. The term includes all of the dodecenyl, undecenyl, decenyl, nonenyl, octenyl, heptenyl, hexenyl, pentenyl, and butenyl isomers, 1-propenyl, 2-propenyl, isopropenyl, and ethenyl. "$C_2$–$C_8$ alkenyl" refers to a $C_2$ to $C_8$ linear or branched alkenyl group. The term includes all of the octenyl, heptenyl, hexenyl, pentenyl, and butenyl isomers, 1-n-propenyl, 2-n-propenyl, isopropenyl, and ethenyl.

"$C_3$–$C_8$ cycloalkyl" means a cyclic ring of an alkane having three to eight total carbon atoms (i.e., cyclopropyl, cyclobutyl, cyclopentyl, cyclohexyl, cycloheptyl or cyclooctyl). "$C_3$–$C_6$ cycloalkyl" refers to a cyclic ring selected from cyclopropyl, cyclobutyl, cyclopentyl, and cyclohexyl; and "$C_5$–$C_7$ cycloalkyl" refers to a cyclic ring selected from cyclopentyl, cyclohexyl, and cycloheptyl.

"$C_4$–$C_{20}$ alkylcycloalkyl" means a $C_3$–$C_8$ cycloalkyl as defined above substituted with one or more $C_1$–$C_8$ alkyl groups as defined above, wherein the total number of carbon atoms in the alkylcycloalkyl group is in the range of from 4 to 20. "$C_6$–$C_{14}$ alkylcycloalkyl" means a $C_5$–$C_7$ cycloalkyl as defined above substituted with one or more $C_1$–$C_6$ alkyl groups as defined above, wherein the total number of carbon atoms in the alkylcycloalkyl group is in the range of from 6 to 14. Representative examples include methylcyclohexyl (i.e., 2-, 3- and 4-methylcyclohexyl), ethylcyclohexyl, methylcyclopentyl, dimethylcyclohexyl (i.e., 2,3-, 2,4-, 2,5-, 2,6-, 3,4-, and 3,5-dimethylcyclohexyl), methylcyclobutyl, and so forth.

"$C_4$–$C_{20}$ cycloalkyl-alkyl" means a $C_1$–$C_8$ alkyl group as defined above substituted with one or more $C_3$–$C_8$ cycloalkyls as defined above, wherein the total number of carbon atoms in the cycloalkyl alkyl group is in the range of from 4 to 20. "$C_6$–$C_{14}$ cycloalkyl-alkyl" means a $C_1$–$C_6$ alkyl group as defined above substituted with one or more $C_5$–$C_7$ cycloalkyl groups as defined above, wherein the total number of carbon atoms in the alkylcycloalkyl group is in the range of from 5 to 14. Representative examples include cyclohexylmethyl, 1- and 2-cyclohexylethyl, cyclohexylisopropyl, 1- and 3-cyclohexyl-n-propyl, dicyclohexylmethyl, and so forth.

"$C_5$–$C_8$ cycloalkenyl" means a cyclic ring of an alkene having five to eight total carbon atoms (i.e., cyclopentenyl, cyclohexenyl, cycloheptenyl or cyclooctenyl). "$C_5$–$C_7$ cycloalkenyl" refers to a cyclic ring selected from cyclopentenyl, cyclohexenyl, and cycloheptenyl.

"$C_6$–$C_{20}$ alkylcycloalkenyl" means a $C_5$–$C_8$ cycloalkenyl as defined above substituted with one or more $C_1$–$C_8$ alkyl groups as defined above, wherein the total number of carbon atoms in the alkylcycloalkyl group is in the range of from 6 to 20. "$C_6$–$C_{16}$ alkylcycloalkenyl" means a $C_5$–$C_7$ cycloalkenyl as defined above substituted with one or more $C_1$–$C_6$ alkyl groups as defined above, wherein the total number of carbon atoms in the alkylcycloalkyl group is in the range of from 6 to 16. Representative examples include methylcyclohexenyl, ethylcyclohexenyl, dimethylcyclohexenyl, methylcycloheptenyl, and so forth.

"$C_6$–$C_{20}$ cycloalkenylalkyl" means a $C_1$–$C_8$ alkyl group as defined above substituted with one or more $C_5$–$C_8$ cycloalkenyl groups as defined above, wherein the total number of carbon atoms in the cycloalkenylalkyl group is in the range of from 6 to 20. "$C_6$–$C_{16}$ cycloalkenylalkyl" means a $C_1$–$C_6$ alkyl group as defined above substituted with one or more $C_5$–$C_7$ cycloalkenyl groups as defined above, wherein the total number of carbon atoms in the cycloalkenylalkyl group is in the range of from 6 to 16. Representative examples include (3- and 4-cyclohexenyl)methyl, (3- and 4-cyclohexenyl)1- and 2-ethyl, and so forth.

"$C_6$–$C_{10}$ aryl" means a group selected from phenyl, biphenyl and naphthyl. The term "biphenyl" includes 2-, 3-, and 4-biphenyl; the term "naphthyl" includes 1- and 2-naphthyl.

"$C_7$–$C_{20}$ alkylaryl" means a $C_6$–$C_{10}$ aryl group as defined above substituted with one or more $C_1$–$C_8$ alkyl groups as defined above, wherein the total number of carbon atoms in the alkylaryl group is in the range of from 7 to 20. Similarly, "$C_7$–$C_{12}$ alkylaryl" means a $C_6$–$C_{10}$ aryl group as defined above substituted with one or more $C_1$–$C_6$ alkyl groups as defined above, wherein the total number of carbon atoms in the alkylaryl group is in the range of from 7 to 12. Representative examples of such alkylaryl groups are 2-, 3- and 4-tolyl; 2-, 3-, and 4-ethylphenyl; 2-methyl-4-ethylphenyl; 4-isopropylphenyl; 2'-methyl-4-biphenyl; and 2-methyl-1-naphthyl.

"$C_7$–$C_{20}$ alkylphenyl" means a phenyl group substituted with one or more $C_1$–$C_6$ alkyl groups as defined above, wherein the total number of carbon atoms in the alkylaryl group is in the range of from 7 to 20.

"$C_8$–$C_{20}$ alkenylaryl" means a $C_6$–$C_{10}$ aryl group as defined above substituted with one or more $C_2$–$C_8$ alkenyl groups as defined above, wherein the total number of carbon atoms in the alkylaryl group is in the range of from 8 to 20. Representative examples of such alkenylaryl groups are 2- and 4-ethenylphenyl and 4-(2-propenyl)phenyl.

"$C_7$–$C_{20}$ arylalkyl" means a $C_1$–$C_8$ alkyl group as defined above substituted with one or more $C_6$–$C_{10}$ aryl groups as defined above, wherein the total number of carbon atoms in the arylalkyl group is in the range of from 7 to 20. Representative examples of such arylalkyl groups are benzyl, 2- and 4-ethylbenzyl, 4-isobutylbenzyl, 2-phenylethyl, 2,2-diphenylethyl, and 2-phenylpropyl.

"$C_7$–$C_{12}$ phenylalkyl" means a $C_1$–$C_6$ alkyl group as defined above substituted with a phenyl group; e.g., benzyl.

The term "heterocyclic" refers to a stable 5- to 7-membered monocyclic ring system which may be saturated or unsaturated, and which consists of carbon atoms and from one to three heteroatoms selected from N, O or S, and wherein the nitrogen and sulfur heteroatoms may optionally be oxidized, and the nitrogen heteroatom may optionally be quaternized. The heterocyclic ring may be attached at any heteroatom or carbon atom which results in the creation of a stable structure. Examples of such heterocyclic groups include, but are not limited to, piperidinyl, piperazinyl, oxopiperazinyl, oxopiperidinyl, oxopyrrolidinyl, oxoazepinyl, azepinyl, pyrrolyl, pyrrolidinyl, furanyl, thienyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isooxazolyl, isoxazolidinyl, morpholinyl, thiazolyl, thiazolidinyl, isothiazolyl, thiadiazolyl, tetrahydropyranyl, thiamorpholinyl, thiamorpholinyl sulfoxide, thiamorpholinyl sulfone, and oxadiazolyl. Morpholino is the same as morpholinyl.

The term "thienyl," as used herein, refers to the group

The terms "substituted $C_{10}$–$C_{12}$ alkyl," "substituted $C_2$–$C_{12}$ alkenyl," "substituted $C_3$–$C_8$ cycloalkyl," "substituted $C_4$–$C_{20}$ alkylcycloalkyl," "substituted $C_4$–$C_{20}$ cycloalkyl-alkyl", "substituted $C_5$–$C_8$ cycloalkenyl," "substituted $C_6$–$C_{20}$ alkylcycloalkenyl," "substituted $C_6$–$C_{20}$ cycloalkenylalkyl," "substituted $C_6$–$C_{10}$ aryl," "substituted $C_7$–$C_{20}$ alkylaryl," "substituted $C_7$–$C_{20}$ alkylphenyl", "substituted $C_8$–$C_{20}$ alkenylaryl," "substituted $C_7$–$C_{20}$ arylalkyl", and "substituted heterocyclic" respectively mean $C_1$–$C_{12}$ alkyl, $C_2$–$C_{12}$ alkenyl, $C_3$–$C_8$ cycloalkyl, $C_4$–$C_{20}$ alkylcycloalkyl, $C_4$–$C_{20}$ cycloalkyl-alkyl, $C_5$–$C_8$ cycloalkenyl, $C_6$–$C_{20}$ alkylcycloalkenyl, $C_6$–$C_{20}$ cycloalkenylalkyl, $C_6$–$C_{10}$ aryl, $C_7$–$C_{20}$ alkylaryl, $C_8$–$C_{20}$ alkenylaryl, $C_7$–$C_{20}$ arylalkyl, and heterocyclic all as defined above, substituted with one or more named substituents (e.g., with one or more of halogen, hydroxy, $(CH_2)_{0-2}OR^7$, nitro, cyano, $(CH_2)_{0-2}COOR^7$, $COR^7$, $(CH_2)_{0-2}CON(R^7)_2$, and $N(R^7)_2$, wherein $R^7$ is $C_1$–$C_6$ alkyl as defined above).

The term "substituted $C_7$–$C_{12}$ phenylalkyl" means a $C_7$–$C_{12}$ phenylalkyl group as defined above substituted with one or more named substituents (e.g., with one or more of halogen, hydroxy, $(CH_2)_{0-2}OR^7$, nitro, cyano, $(CH_2)_{0-2}COOR^7$, $COR^7$, $(CH_2)_{0-2}CON(R^7)_2$, and $N(R^7)_2$, wherein $R^7$ is $C_1$–$C_6$ alkyl as defined above).

The term "carboxylic acid $C_1$–$C_8$ alkyl ester" means —C(=O)OR wherein R is a $C_1$–$C_8$ alkyl group as defined above.

The term "carboxylic acid substituted $C_1$–$C_8$ alkyl ester" means —C(=O)OR$^{subst'd}$ wherein R$^{subst'd}$ is a $C_1$–$C_8$ substituted alkyl group as defined above.

The term "halogen" (alternatively "halo") refers to fluorine, chlorine, bromine, and iodine (alternatively fluoro, chloro, bromo, and iodo).

The term "halogenated $C_1$–$C_{12}$ alkyl" (alternatively "$C_1$–$C_{12}$ haloalkyl") means a $C_1$ to $C_{12}$ linear or branched alkyl group as defined above substituted with one or more halogens. The terms "halogenated $C_1$–$C_8$" and "halogenated $C_1$–$C_6$" have analogous meanings. Representative examples of suitable halo-substituted alkyls include trifluoromethyl, tribromomethyl, 1-fluoroethyl, 2-fluoroethyl, 2,2-difluoroethyl, 2,2,2-trifluoroethyl, 2-bromoethyl, 3,3,3-trifluoro-n-propyl, 3,3,3-trifluoroisopropyl, 1,1,1,3,3,3-hexafluoroisopropyl, and perfluorohexyl.

The term "halogenated $C_2$–$C_{12}$ alkenyl" (alternatively "$C_2$–$C_{12}$ haloalkenyl")means a $C_2$–$C_{12}$ linear or branched alkenyl group as defined above substituted with one or more halogens.

The term "halogenated $C_3$–$C_8$ cycloalkyl" (alternatively "$C_3$–$C_8$ halocycloalkyl")means a cycloalkyl group as defined above substituted with one or more halogens. Representative examples of suitable halogenated cycloalkyls include all isomers of fluorocyclohexyl (i.e., 1-, 2-, 3-, and 4-fluorocyclohexyl), difluorocyclohexyl (e.g., 2,4-difluorocyclohexyl, 3,4-difluorocyclohexyl, etc.), bromocyclohexyl, fluorocyclopentyl, and so forth.

The term "halogenated $C_4$–$C_{20}$ alkylcycloalkyl" means an alkylcycloalkyl group as defined above substituted with one or more halogens. Representative examples include 2-, 3-, and 4-trifluoromethylcyclohexyl; 2-, 3- and 4-trichloromethylcyclohexyl; 2-trifluoromethyl-4-fluorocyclohexyl; 2-, 3- and 4-(2,2,2-trifluoroethyl) cyclohexyl; and so forth.

The term "halogenated $C_4$–$C_{20}$ cycloalkyl-alkyl" means a cycloalkyl-alkyl group as defined above substituted with one or more halogens. Representative examples include cyclohexyltrifluoromethyl, cyclopentyltrifluoromethyl, (4-fluorocyclohexyl-trifluoromethyl, and so forth.

The term "halogenated $C_6$–$C_{10}$ aryl" (alternatively "$C_6$–$C_{10}$ haloaryl")means an aryl group as defined above substituted with one or more halogens. Representative examples include 2-, 3- and 4-fluorophenyl; 2-, 3-, and 4-chlorophenyl; 2,4-difluoro and 2,4-dichlorophenyl; 2,3,4-trifluorophenyl; 4'-chloro-4-biphenyl; 2-chloro-1-naphthyl; and 4-bromo-2-naphthyl.

The term "halogenated $C_7$–$C_{20}$ alkylaryl" means a $C_7$–$C_{20}$ alkylaryl group as defined above substituted with one or more halogens. Representative examples include 2-, 3-, and 4-trifluoromethylphenyl; 2,4-trifluoromethylphenyl; 2-, 3- and 4-fluoromethyl or chloromethyl phenyl; and 2-, 3-, and 4-(2,2,2-trifluoroethyl)phenyl. "Halogenated $C_7$–$C_{12}$ alkylaryl" means a $C_7$–$C_{12}$ alkylaryl as defined above with one or more halogen substituents.

It is understood that the definition of a substituent (e.g., $(CH_2)_{0-2}CO_2R^7$) or variable (e.g., $R^7$) at a particular location in a molecule is independent of its definitions at other locations in that molecule. Thus, for example, in the olefin of Formula (III), when $R^3$ is substituted aryl having the substituent $OR^7$=methoxy, $R^4$ can be substituted aryl having the substituent $OR^7$=methoxy, ethoxy, n-propoxy, etc.

It is also understood that the definition of a substituent or variable at a particular location in a molecule is independent of the definition of another occurrence of the same substituent or variable at the same location. Thus, $N(R^7)_2$ wherein $R^7$ is $C_1$–$C_6$ alkyl represents $N(CH_3)_2$, $N(CH_3)(C_2H_5)$, $N(C_2H_5)_2$, $N(C_2H_5)(C_3H_7)$, and so forth.

Where multiple substituents are disclosed or claimed, the substituted compound can be independently substituted by one or more of the disclosed or claimed substituent moieties, singly or plurally.

It is understood that substituents and substitution patterns on the compounds employed in the processes encompassed by the present invention (e.g., olefin compounds) are selected by one of ordinary skill in the art to provide compounds that are chemically stable under the reaction conditions employed and that are capable of conversion to the desired products (i.e., β-hydroxy carbamates and/or oxazolidinones).

Abbreviations used in the instant specification, particularly the Examples, are as follows:

Aq=aqueous
CDI=carbonyl diimidazole
DMF=N,N-dimethylformamide
Et=ethyl
GC=gas chromatography
HPLC=high performance liquid chromatography
IPAc=isopropyl acetate
LDA=lithium diisopropylamide
Me=methyl
MeOH=methanol
MTBE=methyl-tert-butyl ether
SFC=supercritical fluid chromatography
n-BuLi=n-butyllithium
THF=tetrahydrofuran
TLC=thin layer chromatography The following Examples further describe and illustrate the invention and its practice and are not to be construed as limiting the scope or spirit of the invention.

EXAMPLE 1

Preparation of 4(S)-(3,4-difluorophenyl)-5(S)-methyloxazolidin-2-one

Sodium hydroxide (1.57 g, 39.3 mmole) was dissolved at room temperature in 50 ml of water in a reaction flask, and 1 ml of the solution was used to dissolve potassium osmate dihydrate (0.048 g, 0.13 mmole) in a separate vial. 1-Propanol (25 ml) and ethyl carbamate (3.56 g, 40.0 mmole) were added at room temperature to the reaction flask, followed by 1,3-dichloro-5,5-dimethylhydantoin (3.89 g, 19.7 mmole), and the solids were dissolved at room temperature in approximately 5 minutes. A solution of $(DHQ)_2PHAL$ (0.125 g) and trans-1-(3,4-difluorophenyl)-1-propene (2.0 g, 12.97 mmole) in 25 ml of 1-propanol was then added to the flask, followed by addition of the potassium osmate solution. The reaction (i.e., oxidation) was conducted at about 20° C., with its progress monitored by measuring the disappearance of olefin using HPLC. The oxidation was complete within three hours with essentially 100% conversion. A mixture of the hydroxy carbamates of formulas (XII) and (XIII) was obtained in a mole ratio of (XII) to (XIII) of about 4:1, as determined by NMR or by HPLC.

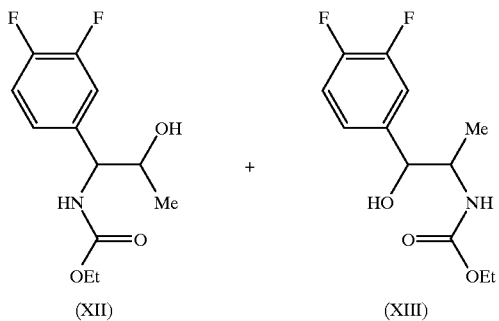

Following the oxidation, sodium hydroxide (2 g) was added to the flask at room temperature. After 30 minutes, the reaction mixture was diluted with water (50 ml) and extracted with 2×50 ml of ethyl acetate. The organic layers were combined and concentrated by rotary evaporation, and the oxazolidinone product was purified by column chromatography. The product was a pale yellow oil and was determined to have 90% enantiomeric excess ("ee") by SFC.

$^1$H NMR $(CDCl_3)=\delta$ 7.19 (m, 2H), 7.08 (m, 1H), 5.58 (s, 1H), 4.41 (m, 2H), 1.51 (d, J=5.9 Hz, 3H).

EXAMPLE 2

Preparation of 4(R)-(3,4-difluorophenyl)-5(R)-methyloxazolidin-2-one

The title compound (pale yellow oil, 90% ee) was obtained using the same procedure as described in Example 1, except that $(DHQD)_2PHAL$ was used instead of $(DHQ)_2PHAL$.

$^1$H NMR $(CDCl_3)=\delta$ 7.19 (m, 2H), 7.08 (m, 1H), 5.58 (s, 1H), 4.41 (m, 2H), 1.51 (d, J=5.9 Hz, 3H).

EXAMPLE 3

Preparation of 4(S)-(phenyl)-5(S)-methyloxazolidin-2-one

The title compound (pale yellow oil, 90% ee) was obtained using the same procedure as described in Example 1, except that trans-β-methylstyrene was used instead of trans-1-(3,4-difluorophenyl)-1-propene.

$^1$H NMR $(CD_3CN)=\delta$ 7.41 (m, 5H), 6.16 (s, 1H), 4.49 (dd, J=7.0, 1.0 Hz, 1H), 4.36 (m, 1H), 1.44 (d, J=6.0 Hz, 3H).

EXAMPLE 4

Preparation of 5(S)-(3,4-difluorophenyl)-4(R)-methyloxazolidin-2-one

The title compound was obtained using the same procedure as described in Example 1, except that acetonitrile is used instead of 1-propanol and $(DHQ)_2AQN$ is used instead of $(DHQ)_2PHAL$, which upon completion of the oxidation step provided a mixture of the hydroxy carbamates (XII) and (XIII) in a mole ratio of (XII) to (XIII) of about 1:1.7.

EXAMPLE 5

Preparation of 4(S)-(3,4-difluorophenyl)-5(S)-methyloxazolidin-2-one

Using the same procedure as described in Example 1 for the oxidation of trans-1-(3,4-difluorophenyl)-1-propene, a mixture of hydroxy carbamates (XII) and (XIII) was obtained in a mole ratio of (XII) to (XIII) of about 4:1.

Recovery Procedure A. Sodium hydroxide (2 g) was added to a portion of the mixture, and after 30 minutes at room temperature the reaction mixture was diluted with water (50 ml) to obtain a mixture of oxazolidinones including the title compound, a minor portion of the enantiomer of the title compound, and the 4-methyl-5-(3,4-difluorophenyl) oxazolidin-2-one enantiomers (with the 4(S)-methyl-5(S)-(3,4-difluorophenyl)oxazolidin-2-one being the predominant enantiomer). The title compound (90% ee) was recovered from the oxazolidinone mixture by extraction with MTBE, followed by separation via flash chromatography using a silica column.

Recovery Procedure B. Cesium carbonate (2 g) was added to another portion of the hydroxy carbamate mixture, and after about thirty minutes at room temperature the reaction mixture was diluted with water (50 ml). Sulfuric acid (10 eq.) was then added, and the mixture was refluxed for 30 minutes to obtain a mixture of the title compound plus 1-(3,4-difluorophenyl)-2-hydroxy-propylamine. Isolation by neutralization with NaOH to a pH=8–9, and extraction with MTBE afforded the title compound, which was obtained in 90% ee by evaporative removal of the MTBE.

EXAMPLE 6

3-[4-(4-Fluorophenyl)piperidin-1-yl]propylamine

Step A. 4-(4-Fluorophenyl)piperidine hydrochloride

To a solution of 4-(4-fluorophenyl)-1,2,3,6-tetrahydropyridine hydrochloride (10 g) in methanol (200 mL) was added 10% palladium on charcoal (0.5 g) and the mixture was hydrogenated at 50 psi for 3 h. The catalyst was removed by filtration and solvent was evaporated to leave the product as a white powder, which was used in the next step without any purification.

M.P. 181–182° C. $^1$H NMR (CDCl$_3$): δ 1.95–2.03 (br d, 2H), 2.14–2.29 (m, 2H), 2.70–2.80 (m, 1H), 2.91–3.07 (br q, 2H), 3.60–3.64 (br d, 2H), 6.96–7.03 (m, 2H), 7.19–7.22 (m, 2H), 9.60 (br s, 1H), 9.71 (br s, 1H).

Step B. 3-[4-(4-Fluorophenyl)piperidin-1-yl]propylphthalimide

A mixture of 4-(4-fluorophenyl)piperidine hydrochloride (5.08 g, 23.2 mmol), 3-bromopropylphthalimide (6.22 g, 23.2 mmol), and potassium carbonate (15 g) in DMF (100 mL) was stirred and heated at 95–100° C. for 12 h. About 80% of the solvent was evaporated at reduced pressure, the residue was diluted with ethyl acetate (200 mL) and washed with brine (3×100 mL) and dried (Na$_2$SO$_4$). Solvent was evaporated and the residue was purified by column chromatography on silica gel using 1/1 hexane-ethyl acetate to 100% ethyl acetate as eluent. This product was crystallized from isopropanol to give a white crystalline solid; m.p. 80–81° C. This material was used in the next step. Concentration of the mother liquor and cooling gave the second crop.

$^1$H NMR (CDCl$_3$): δ 1.43–1.52 (m, 2H), 1.67–1.75 (m, 2H), 1.80–1.96 (m, 4H), 2.33–2.46 (m, 3H), 2.94–2.99 (br d, 2H), 3.78 (t, J=7 Hz, 2H), 6.90–7.04 (m, 4H), 7.70–7.74 (m, 2H), 7.84–7.87 (m, 2H).

Step C. 3-[4-(4-Fluorophenyl)piperidin-1-yl]propylamine

To a solution of 3-[4-(4-fluorophenyl)piperidin-1-yl] propylphthalimide (4.5 g, 12.3 mmol) in methanol (200 mL) was added 4 ml of hydrazine and the mixture was refluxed for 8 h. It was cooled, and the white solid was filtered and washed with methanol (20 mL). Solvent was evaporated, and the residue was dried under vacuum for 4 h. Chloroform (50 mL) was added to this material, it was stirred for 1 h and filtered. The white solid was washed with more chloroform (20 mL), and the solvent was evaporated from the combined filtrates to leave the crude product as an oil. It was purified by column chromatography on silica gel using dichloromethane/methanol/2M ammonia in methanol (10/3/1) as the eluent.

$^1$H NMR (CDCl$_3$): δ 1.60–1.83 (m, 6H), 1.96–2.07 (m, 4H), 2.40–2.55 (m, 3H), 2.70–2.85 (br t, 2H), 3.03–3.07 (br d, 2H), 6.93–7.00 (m, 2H), 7.14–7.20 (m, 2H).

EXAMPLE 7

Preparation of (4S,5S)-4-(3,$^4$-Difluorophenyl)-N-[3-[4-(4-fluorophenyl)- 1-piperidinyl]propyl]-5-methyl-2-oxo-3-oxazolidine carboxamide

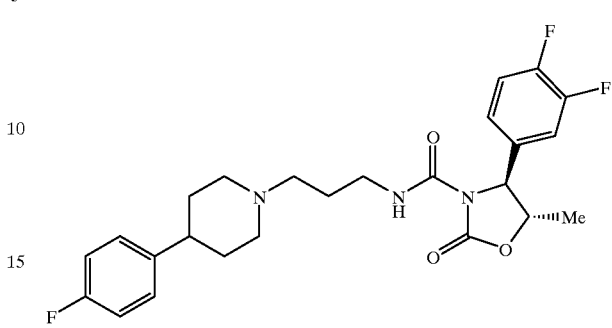

Procedure 1: 4(S)-(3,4-difluorophenyl)-5(S)-methyloxazolidin-2-one (2 g, 9.4 mmole) was dissolved in THF (20 ml) and cooled to −60 C for the dropwise addition of n-BuLi (4 ml, 2.5 M in hexane). In a separate flask, p-nitrophenyl chloroformate was dissolved in 20 ml THF and cooled to −60 C. When the addition of n-BuLi was complete, the mixture was aged at −60 C for 30 minutes. and then transferred via cannula to the p-nitrophenyl chloroformate solution. The reaction mixture was then allowed to warm to room temperature, and reaction progress was monitored by HPLC. After 2.5 hours, 3-(4-(4-fluorophenyl)piperidin-1-yl) propylamine (Example 6) (2.2 g, 9.4 mmole) in THF was added. After 3.5 hours at room temperature age, the solution was diluted with 100 ml water and extracted with 2×50 ml MTBE. The MTBE extractions were combined and washed with 2×50 ml 1M sulfuric acid. The aqueous washes were combined, rendered basic (pH=9–10) with 2 M sodium carbonate, and extracted with 2×100 ml MTBE. The MTBE layers were combined and concentrated, and the title compound was isolated by column chromatography on silica gel using 9:1 EtOAc: MeOH.

Procedure 2: A 250 ml 3 neck round bottom flask was charged with 4(S)-(3,4-difluorophenyl)-5(S)-methyloxazolidin-2-one (1.10 g, 5.2 mmole) and cooled to −65 C. n-BuLi (2.5 ml, 2.5 M) was then added dropwise over 5 minutes. CDI was added as a solid in a single portion, and the reaction mixture was warmed to room temperature. After 2 hours, 3-(4-(4-fluorophenyl)piperidin-1-yl) propylamine (2.0 g, 8.5 mmole) was added and the reaction mixture was aged at room temperature for 16 hours. The mixture was diluted with 50 ml water, and extracted with 2×50 ml IPAc, concentrated to an oil, and the title compound was isolated by column chromatography in the manner described in Procedure 1.

While the foregoing specification teaches the principles of the present invention, with examples provided for the purpose of illustration, the practice of the Ace invention encompasses all of the usual variations, adaptations, modifications, deletions or additions of procedures and protocols described herein, that fall within the scope of the following claims.

What is claimed is:

1. A process for preparing a β-hydroxy carbamate product which comprises reacting an olefin compound containing at least one carbon-carbon double bond with a carbamate in an aqueous solvent and in the presence of a base, an osmium catalyst, a co-oxidant, and optionally an asymmetric ligand, to form a reaction mixture containing the β-hydroxy carbamate product; wherein the co-oxidant is (1) a hydantoin is of Formula (Ia):

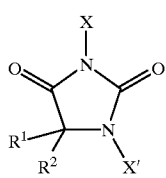

(Ia)

wherein X and X' are each independently H, Cl, or Br, and at least one of X and X' is Cl or Br; $R^1$ and $R^2$ are each independently selected from H, $C_1$–$C_6$ alkyl, $C_3$–$C_8$ cycloalkyl, $C_4$–$C_{20}$ alkylcycloalkyl, and $C_4$–$C_{20}$ cycloalkyl-alkyl; or (2) an isocyanuric acid of Formula (Ib):

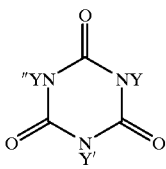

(Ib)

or an alkali metal salt thereof; wherein Y, Y' and Y" are each independently H, Cl, or Br, and at least one of Y, Y' and Y" is Cl or Br.

2. The process according to claim 1, wherein the olefin compound is selected from the group consisting of mono-substituted, 1,1-disubstituted, trans-disubstituted, and trisubstituted olefins, wherein each substituent is independently $C_1$–$C_{18}$ hydrocarbyl, substituted $C_1$–$C_{18}$ hydrocarbyl, carboxylic acid $C_1$–$C_8$ hydrocarbyl ester, or carboxylic acid substituted $C_1$–$C_8$ hydrocarbyl ester.

3. The process according to claim 1, wherein the olefin compound is a compound of formula (III):

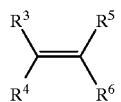

(III)

wherein $R^3$, $R^4$, $R^5$ and $R^6$ are each independently selected from hydrogen, $C_1$–$C_{12}$ alkyl, $C_2$–$C_{12}$ alkenyl, $C_3$–$C_8$ cycloalkyl, $C_4$–$C_{20}$ alkylcycloalkyl, $C_4$–$C_{20}$ cycloalkyl-alkyl, $C_5$–$C_8$ cycloalkenyl, $C_6$–$C_{20}$ alkylcycloalkenyl, $C_6$–$C_{20}$ cycloalkenylalkyl, $C_6$–$C_{10}$ aryl, $C_7$–$C_{20}$ alkylaryl, $C_8$–$C_{20}$ alkenylaryl, $C_7$–$C_{20}$ arylalkyl, heterocyclic, carboxylic acid $C_1$–$C_8$ alkyl ester, substituted $C_1$–$C_{12}$ alkyl, substituted $C_2$–$C_{12}$ alkenyl, substituted $C_3$–$C_8$ cycloalkyl, substituted $C_4$–$C_{20}$ alkylcycloalkyl, substituted $C_4$–$C_{20}$ cycloalkyl-alkyl, substituted $C_5$–$C_8$ cycloalkenyl, substituted $C_6$–$C_{20}$ alkylcycloalkenyl, substituted $C_6$–$C_{20}$ cycloalkenylalkyl, substituted $C_6$–$C_{10}$ aryl, substituted $C_7$–$C_{20}$ alkylaryl, substituted $C_8$–$C_{20}$ alkenylaryl, substituted $C_7$–$C_{20}$ arylalkyl, substituted heterocyclic, and carboxylic acid substituted $C_1$–$C_8$ alkyl ester, wherein the substituents therefor are independently selected from halogen, hydroxy, $(CH_2)_{0-2}OR^7$, nitro, cyano, $(CH_2)_{0-2}COOR^7$, $COR^7$, $(CH_2)_{0-2}CON(R^7)_2$, and $N(R^7)_2$; or $R^3$ and $R^4$ together with the carbon atom to which they are attached form a 5- to 10-membered monocyclic or bicyclic saturated or unsaturated carbocyclic ring system which is optionally substituted with one or more of $C_1$–$C_8$ alkyl, halogen, hydroxy, and $(CH_2)_{0-2}OR^7$; and $R^5$ and $R^6$ are as defined above; or $R^3$ and $R^5$ together with each of the carbon atoms of the carbon-carbon double bond form a 5- to 10-membered monocyclic or bicyclic unsaturated carbocyclic ring system which is optionally substituted with one or more of $C_1$–$C_8$ alkyl, halogen, hydroxy, and $(CH_2)_{0-2}OR^7$; and $R^4$ and $R^6$ are each independently selected from hydrogen, $C_1$–$C_{12}$ alkyl, $C_2$–$C_{12}$ alkenyl, $C_3$–$C_8$ cycloalkyl, $C_4$–$C_{20}$ alkylcycloalkyl, $C_5$–$C_8$ cycloalkenyl, $C_6$–$C_{20}$ alkylcycloalkenyl, $C_6$–$C_{10}$ aryl, $C_7$–$C_{20}$ alkylaryl, $C_8$–$C_{20}$ alkenylaryl, $C_7$–$C_{20}$ arylalkyl, heterocyclic, carboxylic acid $C_1$–$C_8$ alkyl ester, substituted $C_1$–$C_{12}$ alkyl, substituted $C_2$–$C_{12}$ alkenyl, substituted $C_3$–$C_8$ cycloalkyl, substituted $C_4$–$C_{20}$ alkylcycloalkyl, substituted $C_5$–$C_8$ cycloalkenyl, substituted $C_6$–$C_{20}$ alkylcycloalkenyl, substituted $C_6$–$C_{10}$ aryl, substituted $C_7$–$C_{20}$ alkylaryl, substituted $C_8$–$C_{20}$ alkenylaryl, substituted $C_7$–$C_{20}$ arylalkyl, substituted heterocyclic, and carboxylic acid substituted $C_1$–$C_8$ alkyl ester, wherein the substituents therefor are independently selected from halogen, hydroxy, $(CH_2)_{0-2}OR^7$, nitro, cyano, $(CH_2)_{0-2}COOR^7$, $COR^7$, $(CH_2)_{0-2}CON(R^7)_2$, and $N(R^7)_2$; or $R^3$ and $R^4$ together with the carbon atom to which they are attached form one 5- to 10-membered monocyclic or bicyclic saturated or unsaturated carbocyclic ring system; and $R^5$ and $R^6$ together with the carbon atom to which they are attached form a second 5 to 10 membered monocyclic or bicyclic saturated or unsaturated carbocyclic ring system, wherein each ring system is optionally substituted with one or more of $C_1$–$C_8$ alkyl, halogen, hydroxy, and $(CH_2)_{0-2}OR^7$; and $R^7$ is $C_1$–$C_6$ alkyl.

4. The process according to claim 3, wherein the olefin compound is a trans-disubstituted olefin compound, wherein $R^3$ and $R^6$ are hydrogen;

$R^4$ and $R^5$ are each independently selected from $C_1$–$C_{12}$ alkyl, $C_2$–$C_{12}$ alkenyl, $C_3$–$C_8$ cycloalkyl, $C_4$–$C_{20}$ alkylcycloalkyl, $C_5$–$C_8$ cycloalkenyl, $C_6$–$C_{20}$ alkylcycloalkenyl, $C_6$–$C_{10}$ aryl, $C_7$–$C_{20}$ alkylaryl, $C_8$–$C_{20}$ alkenylaryl, $C_7$–$C_{20}$ arylalkyl, heterocyclic, carboxylic acid $C_1$–$C_8$ alkyl ester, substituted $C_1$–$C_{12}$ alkyl, substituted $C_2$–$C_{12}$ alkenyl, substituted $C_3$–$C_8$ cycloalkyl, substituted $C_4$–$C_{20}$ alkylcycloalkyl, substituted $C_5$–$C_8$ cycloalkenyl, substituted $C_6$–$C_{20}$ alkylcycloalkenyl, substituted $C_6$–$C_{10}$ aryl, substituted $C_7$–$C_{20}$ alkylaryl, substituted $C_8$–$C_{20}$ alkenylaryl, substituted $C_7$–$C_{20}$ arylalkyl, substituted heterocyclic, and carboxylic acid substituted $C_1$–$C_8$ alkyl ester, wherein the substituents therefor are independently selected from halogen, hydroxy, $(CH_2)_{0-2}OR^7$, nitro, cyano, $(CH_2)_{0-2}COOR^7$, $COR^7$, $(CH_2)_{0-2}CON(R^7)_2$, and $N(R^7)_2$.

5. The process according to claim 4, wherein $R^4$ is $C_6$–$C_{10}$ aryl, $C_7$–$C_{12}$ alkylaryl, halogenated $C_6$–$C_{10}$ aryl, or halogenated $C_7$–$C_{12}$ alkylaryl; and $R^5$ is $C_1$–$C_6$ alkyl, halogenated $C_1$–$C_6$ alkyl, or carboxylic acid $C_1$–$C_6$ alkyl ester.

6. The process according to claim 1, wherein the aqueous solvent comprises water and a water-soluble co-solvent.

7. The process according to claim 1, wherein the carbamate is of Formula (IV):

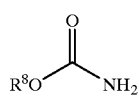

wherein $R^8$ is selected from $C_1$–$C_{20}$ hydrocarbyl and substituted $C_1$–$C_{20}$ hydrocarbyl.

8. The process according to claim 1, wherein the base is selected from alkali metal hydroxides and alkali metal carbonates.

9. The process according to claim 1, wherein the asymmetric ligand is selected from $(DHQ)_2PHAL$, $(DHQD)_2PHAL$, $(DHQ)_2AQN$, and $(DHQD)_2AQN$.

10. The process according to claim 1, wherein the osmium catalyst is $K_2[OsO_2(OH)_4]$.

11. The process according to claim 1, wherein the co-oxidant is selected from 1,3-dichloro-5,5-dimethylhydantoin, 1,3-dibromo-5,5-dimethylhydantoin, 1-bromo-3-chloro-5,5-dimethylhydantoin, 3-bromo-1-chloro-5,5-dimethylhydantoin, 1,3-dichloro-5-methyl-5-isopropylhydantoin, trichloroisocyanuric acid, dichloroisocyanuric acid, and sodium dichloroisocyanurate.

12. The process according to claim 1, further comprising treating the reaction mixture with additional base to form at least one oxazolidinone.

13. The process according to claim 12, further comprising recovering the oxazolidinone from the reaction mixture.

14. The process according to claim 13, further comprising treating the recovered oxazolidinone with a deprotonation agent; contacting the treated oxazolidinone with a formylating agent to provide a formulated intermediate; and then contacting the formulated intermediate with a primary or secondary amine to obtain a coupled amine product.

15. The process according to claim 4, further comprising treating the reaction mixture with additional base to form an oxazolidinone of Formula (V):

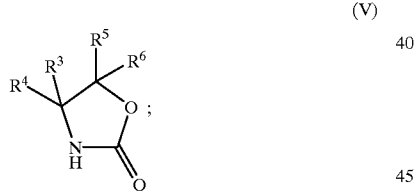

wherein $R^3$, $R^4$, $R^5$ and $R^6$ are as heretofore defined, except that when $R^3$ and $R^5$ together with the carbon atoms to which they are attached form a 5- to 10-membered monocyclic or bicyclic carbocyclic ring system, the ring system is saturated or unsaturated.

16. The process according to claim 15, further comprising recovering the oxazolidinone from the reaction mixture.

17. The process according to claim 16, wherein the additional base used to form the oxazolidinone is an alkali metal carbonate and recovering comprises acidifying the reaction mixture, neutralizing the acidified mixture with base, and extracting the oxazolidinone with organic solvent.

18. The process according to claim 1, wherein the olefin compound is characterized by the absence of a $C_2$ axis of symmetry parallel to the double bond, the reaction mixture includes the asymmetric ligand, and the product is an asymmetric β-hydroxy carbamate.

19. The process according to claim 18, further comprising treating the reaction mixture with additional base to form an asymmetric oxazolidinone, and recovering the asymmetric oxazolidinone.

20. The process according to claim 19, wherein the additional base used to form the asymmetric oxazolidinone is an alkali metal carbonate and recovering comprises acidifying the reaction mixture, neutralizing the acidified mixture with base, and extracting the oxazolidinone with organic solvent.

21. The process according to claim 19, further comprising treating the recovered oxazolidinone with a deprotonation agent; then contacting the treated oxazolidinone with a formylating agent to provide a formulated intermediate; and then contacting the formulated intermediate with a primary or secondary amine to obtain a coupled amine product.

22. A process for preparing an asymmetric oxazolidinone of Formula (V-1):

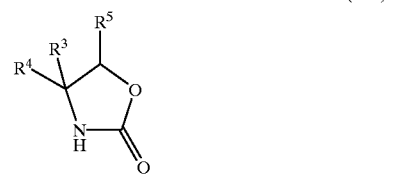

which comprises:

(A) reacting an olefin compound of formula (VI):

in aqueous solvent in the presence of a base, an osmium catalyst, an asymmetric ligand, and a co-oxidant to form a reaction mixture containing an asymmetric β-hydroxy carbamate product; and (B) contacting the reaction mixture with additional base to form the oxazolidinone;

wherein the co-oxidant employed in (A) is (1) a hydantoin is of Formula (Ia):

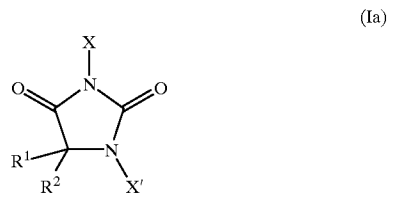

wherein X and X' are each independently H, Cl, or Br, and at least one of X and X' is Cl or Br; $R^1$ and $R^2$ are each independently selected from H, $C_1$–$C_6$ alkyl, $C_3$–$C_8$ cycloalkyl, $C_4$–$C_{20}$ alkylcycloalkyl, and $C_4$–$C_{20}$ cycloalkyl-alkyl; or (2) an isocyanuric acid of Formula (Ib):

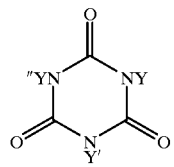

or an alkali metal salt thereof; wherein Y, Y' and Y" are each independently H, Cl, or Br, and at least one of Y, Y' and Y" is Cl or Br; and wherein $R^3$ and $R^4$ are each independently selected from hydrogen, $C_1$–$C_{12}$ alkyl, $C_2$–$C_{12}$ alkenyl, $C_3$–$C_8$ cycloalkyl, $C_4$–$C_{20}$ alkylcycloalkyl, $C_4$–$C_{20}$ cycloalkyl-alkyl, $C_5$–$C_8$ cycloalkenyl, $C_6$–$C_{20}$ alkylcycloalkenyl, $C_6$–$C_{20}$ cycloalkenylalyl, $C_6$–$C_{10}$ aryl, $C_7$–$C_{20}$ alkylaryl, $C_8$–$C_{20}$ alkenylaryl, $C_7$–$C_{20}$ arylalkyl, heterocyclic, carboxylic acid $C_1$–$C_8$ alkyl ester, substituted $C_1$–$C_{12}$ alkyl, substituted $C_2$–$C_{12}$ alkenyl, substituted $C_3$–$C_8$ cycloalkyl, substituted $C_4$–$C_{20}$ alkylcycloalkyl, substituted $C_4$–$C_{20}$ cycloalkyl-alkyl, substituted $C_5$–$C_8$ cycloalkenyl, substituted $C_6$–$C_{20}$ alkylcycloalkenyl, substituted $C_6$–$C_{20}$ cycloalkenylalkyl, substituted $C_6$–$C_{10}$ aryl, substituted $C_7$–$C_{20}$ alkylaryl, substituted $C_8$–$C_{20}$ alkenylaryl, substituted $C_7$–$C_{20}$ arylalkyl, substituted heterocyclic, and carboxylic acid substituted $C_1$–$C_8$ alkyl ester, wherein the substituents thereon are independently selected from halogen, hydroxy, $(CH_2)_{0-2}OR^7$, nitro, cyano, $(CH_2)_{0-2}COOR^7$, $COR^7$, $(CH_2)_{0-2}CON(R^7)_2$, and $N(R^7)_2$; or $R^3$ and $R^4$ together with the carbon atom to which they are attached form a 5- to 10-membered monocyclic or bicyclic saturated or unsaturated carbocyclic ring system which is optionally substituted with one or more of $C_1$–$C_8$ alkyl, halogen, hydroxy, and $(CH_2)_{0-2}OR^7$;

$R^5$ is selected from hydrogen, $C_1$–$C_{12}$ alkyl, $C_2$–$C_{12}$ alkenyl, $C_3$–$C_8$ cycloalkyl, $C_4$–$C_{20}$ alkylcycloalkyl, $C_4$–$C_{20}$ cycloalkyl-alkyl, $C_5$–$C_8$ cycloalkenyl, $C_6$–$C_{20}$ alkylcycloalkenyl, $C_6$–$C_{20}$ cycloalkenylalyl, $C_6$–$C_{10}$ aryl, $C_7$–$C_{20}$ alkylaryl, $C_8$–$C_{20}$ alkenylaryl, $C_7$–$C_{20}$ arylalkyl, heterocyclic, carboxylic acid $C_1$–$C_8$ alkyl ester, substituted $C_1$–$C_{12}$ alkyl, substituted $C_2$–$C_{12}$ alkenyl, substituted $C_3$–$C_8$ cycloalkyl, substituted $C_4$–$C_{20}$ alkylcycloalkyl, substituted $C_4$–$C_{20}$ cycloalkyl-alkyl, substituted $C_5$–$C_8$ cycloalkenyl, substituted $C_6$–$C_{20}$ alkylcycloalkenyl, substituted $C_6$–$C_{20}$ cycloalkenylalkyl, substituted $C_6$–$C_{10}$ aryl, substituted $C_7$–$C_{20}$ alkylaryl, substituted $C_8$–$C_{20}$ alkenylaryl, substituted $C_7$–$C_{20}$ arylalkyl, substituted heterocyclic, and carboxylic acid substituted $C_1$–$C_8$ alkyl ester, wherein the substituents thereon are independently selected from halogen, hydroxy, $(CH_2)_{0-2}OR^7$, nitro, cyano, $(CH_2)_{0-2}COOR^7$, $COR^7$, $(CH_2)_{0-2}CON(R^7)_2$, and $N(R^7)_2$;

$R^7$ is $C_1$–$C_6$ alkyl; and $R^8$ is selected from $C_1$–$C_{20}$ hydrocarbyl and substituted $C_1$–$C_{20}$ hydrocarbyl; provided that (i) at least one of $R^3$, $R^4$, and $R^5$ is not hydrogen; (ii) when $R^3$ is the same as $R^4$, $R^5$ is not hydrogen; and (iii) when $R^3$ and $R^4$ together form a carbocyclic ring system which is symmetrical with respect to a $C_2$ axis bisecting the carbocyclic ring system and also passing through the carbon atom in the oxazolidinone ring to which $R^3$ and $R^4$ are attached, $R^5$ is not hydrogen.

23. The process according to claim 22, wherein $R^3$ is hydrogen.

24. The process according to claim 23, wherein $R^4$ is a group of Formula (VII):

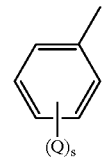

wherein each Q is independently selected from halogen, hydroxy, $C_1$–$C_6$ alkyl, halogenated $C_1$–$C_6$ alkyl, $(CH_2)_{0-2}OR^7$, nitro, cyano, $(CH_2)_{0-2}COOR^7$, $COR^7$, $(CH_2)_{0-2}CON(R^7)_2$, and $N(R^7)_2$;

$R^5$ is selected from hydrogen, $C_1$–$C_6$ alkyl, substituted $C_1$–$C_6$ alkyl, and carboxylic acid $C_1$–$C_6$ alkyl ester; wherein the substituents on the alkyl are independently selected from halogen, hydroxy, and $(CH_2)_{0-2}OR^7$; and s in an integer of from 1 to 3.

25. The process according to claim 22, wherein the aqueous solvent composes water and a water-soluble co-solvent.

26. The process according to claim 22, wherein $R^8$ is selected from $C_1$–$C_6$ alkyl, substituted $C_1$–$C_6$ alkyl, $C_7$–$C_{20}$ arylalkyl, and substituted $C_7$–$C_{20}$ arylalkyl, wherein the substituents thereon are independently selected from halogen, cyano, nitro, and $C_1$–$C_4$ alkoxy.

27. The process according to claim 22, wherein the base is selected from alkali metal hydroxides and alkali metal carbonates.

28. The process according to claim 22, wherein the asymmetric ligand is selected from $(DHQ)_2PHAL$, $(DHQD)_2\ PHAL$, $(DHQ)_2AQN$, and $(DHQD)_2AQN$.

29. The process according to claim 22, wherein the osmium catalyst is $K_2[OsO_2(OH)_4]$.

30. The process according to claim 22, wherein the co-oxidant is selected from 1,3-dichloro-5,5-dimethylhydantoin, 1,3-dibromo-5,5-dimethylhydantoin, 1-bromo-3-chloro-5,5-dimethylhydantoin, 3-bromo-1-chloro-5,5-dimethylhydantoin, 1,3-dichloro-5-methyl-5-isopropylhydantoin, trichloroisocyanuric acid, dichloroisocyanuric acid, and sodium dichloroisocyanurate.

31. The process according to claim 22, which further comprises recovering the oxazolidinone of Formula (V-1).

32. The process according to claim 22, wherein the oxazolidinone is of formula (V-1a):

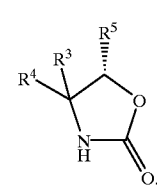

33. The process according to claim 32, which further comprises recovering the oxazolidinone of Formula (V-1a); treating the recovered oxazolidinone with a deprotonation agent; contacting the treated oxazolidinone with a formylating agent to provide a formulated intermediate; and then contacting the formulated intermediate with a primary or secondary amine to obtain a coupled amine product.

34. The process according to claim 33, wherein the amine is a primary amine of Formula (XII):

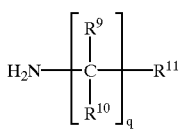

(XII)

wherein $R^9$ and $R^{10}$ are each independently hydrogen, $C_1$–$C_4$ alkyl, or $C_5$–$C_7$ cycloalkyl; $R^{11}$ is

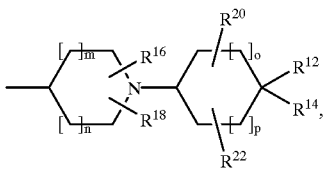

(XIII)

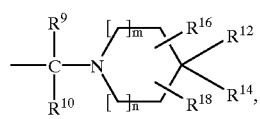

(XIV)

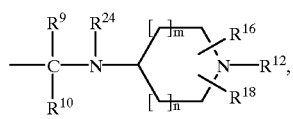

(XV)

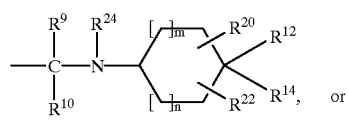

(XVI)

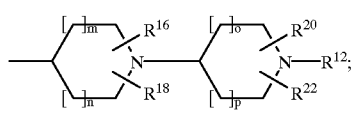

(XVII)

wherein $R^{12}$ is selected from phenyl, substituted phenyl, naphthyl, substituted naphthyl, heterocyclic, or substituted heterocyclic; wherein the substituents on the substituted phenyl or naphthyl are independently selected from halogen, hydroxy, trifluoromethyl, cyano, nitro, $C_1$–$C_4$ alkyl, $C_1$–$C_4$ alkoxy, $NHR^a$, and $N(R^a)_2$; the heterocyclic is pyridyl, pyridyl N-oxide (N->O), pyrazinyl, thienyl, thiazolyl, furanyl, or quinazolinyl; and the substituents on the heterocyclic are independently selected from halogen, trifluoromethyl, cyano, nitro, $C_1$–$C_4$ alkyl, $C_1$–$C_4$ alkoxy, phenyl, $C_3$–$C_4$ cycloalkyl, $NHR^a$, and $N(R^a)_2$; $R^{14}$ is hydrogen, cyano, $C_1$–$C_4$ alkyl, $OR^b$, $CO_2R^b$, $CON(R^a)_2$, phenyl, substituted phenyl, naphthyl, substituted naphthyl, pyridyl, thienyl, furanyl, substituted pyridyl, substituted thienyl, or substituted furanyl; wherein the substituents on the substituted phenyl or naphthyl are independently selected from halogen, trifluoromethyl, cyano, nitro, $C_1$–$C_4$ alkyl, $C_1$–$C_4$ alkoxy, $NHR^a$, and $N(R^a)_2$; and the substituents on the substituted pyridyl, thienyl, or furanyl are independently selected from trifluoromethyl, phenyl, halogen, $C_1$–$C_4$ alkyl, $C_1$–$C_4$ alkoxy, and $C_3$–$C_8$ cycloalkyl;

$R^{16}$, $R^{18}$, $R^{20}$ and $R^{22}$ are each independently selected from hydrogen, $C_1$–$C_{10}$ alkyl, $C_3$–$C_8$ cycloalkyl, $(CH_2)_{0-4}OR^a$, $(CH_2)_{0-4}CF_3$, $(CH_2)_{0-4}CO_2R^a$, $(CH_2)_{0-4}CN$, $(CH_2)_{0-4}NHR^a$, and $(CH_2)_{0-4}N(R^a)_2$;

$R^{24}$ is hydrogen, $C_1$–$C_4$ alkyl, or $C_5$–$C_7$ cycloalkyl;

$R^a$ is $C_1$–$C_4$ alkyl;

$R^b$ is hydrogen, $C_1$–$C_4$ alkyl, $C_3$–$C_8$ cycloalkyl, or $(CH_2)_{1-4}CF_3$;

m, n, o, and p are each independently selected from 0, 1, and 2, with the proviso that the sum of m+n and the sum of o+p are independently never greater than 3; and q is an integer from 0 to 4.

35. The process according to claim 34, wherein the oxazolidinone is 4(S)-(3,4-difluorophenyl)-5(S)-methyloxazolidin-2-one; the primary amine is 3-(4-(4-fluorophenyl)piperidin-1-yl)propylamine; and the coupled amine product is

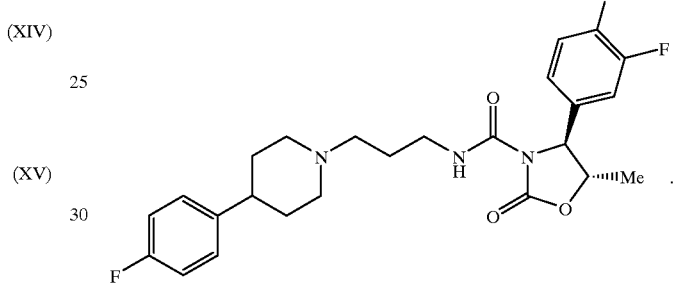

36. The process according to claim 22, wherein the oxazolidinone is of formula (V-1c):

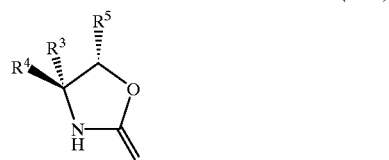

(V-1c)

or of formula (V-1d)

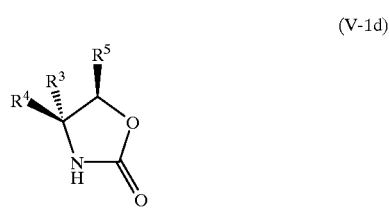

(V-1d)

wherein $R^3$ is hydrogen; $R^4$ is $C_6$–$C_{10}$ aryl, $C_7$–$C_{12}$ alkylaryl, halogenated $C_6$–$C_{10}$ aryl, or halogenated $C_7$–$C_{12}$ alkylaryl; and $R^5$ is hydrogen, $C_1$–$C_6$ alkyl, substituted $C_1$–$C_6$ alkyl, and carboxylic acid $C_1$–$C_6$ alkyl ester, wherein the substituents on the alkyl are independently selected from halogen, hydroxy, and $(CH_2)_{0-2}OR^7$.

37. A process for preparing an oxazolidinone of Formula (V):

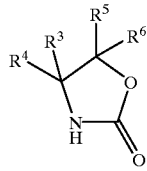

(V)

from a mixture comprising a β-hydroxy carbamate of Formula (VIII):

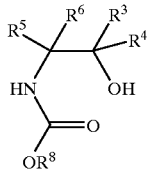

(VIII)

and a β-hydroxy carbamate of Formula (IX):

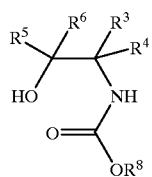

(IX)

which comprises contacting the mixture with an alkali metal carbonate to form the oxazolidinone of Formula (V); acidifying the oxazolidinone-containing mixture to form a hydroxy amine of Formula (XI):

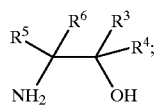

(XI)

neutralizing the mixture with base; and recovering the oxazolidinone by extraction with organic solvent; wherein
$R^3$, $R^4$, $R^5$ and $R^6$ are each independently selected from hydrogen, $C_1$–$C_{12}$ alkyl, $C_2$–$C_{12}$ alkenyl, $C_3$–$C_8$ cycloalkyl, $C_4$–$C_{20}$ alkylcycloalkyl, $C_4$–$C_{20}$ cycloalkyl-alkyl, $C_5$–$C_8$ cycloalkenyl, $C_6$–$C_{20}$ alkylcycloalkenyl, $C_6$–$C_{20}$ cycloalkenylalkyl, $C_6$–$C_{10}$ aryl, $C_7$–$C_{20}$ alkylaryl, $C_8$–$C_{20}$ alkenylaryl, $C_7$–$C_{20}$ arylalkyl, heterocyclic, carboxylic acid $C_1$–$C_8$ alkyl ester, substituted $C_1$–$C_{12}$ alkyl, substituted $C_2$–$C_{12}$ alkenyl, substituted $C_3$–$C_8$ cycloalkyl, substituted $C_4$–$C_{20}$ alkylcycloalkyl, substituted $C_4$–$C_{20}$ cycloalkyl-alkyl, substituted $C_5$–$C_8$ cycloalkenyl, substituted $C_6$–$C_{20}$ alkylcycloalkenyl, substituted $C_6$–$C_{20}$ cycloalkenylalkyl, substituted $C_6$–$C_{10}$ aryl, substituted $C_7$–$C_{20}$ alkylaryl, substituted $C_8$–$C_{20}$ alkenylaryl, substituted $C_7$–$C_{20}$ arylalkyl, substituted heterocyclic, and carboxylic acid substituted $C_1$–$C_8$ alkyl ester, wherein the substituents therefor are independently selected from halogen, hydroxy, $(CH_2)_{0-2}OR^7$, nitro, cyano, $(CH_2)_{0-2}COOR^7$, $COR^7$, $(CH_2)_{0-2}CON(R^7)_2$, and $N(R^7)_2$; or $R^3$ and $R^4$ together form a 5- to 10-membered monocyclic or bicyclic saturated or unsaturated carbocyclic ring system which is optionally substituted with one or more of $C_1$–$C_8$ alkyl, halogen, hydroxy, and $(CH_2)_{0-2}OR^7$; and $R^5$ and $R^6$ are as defined above; or $R^3$ and $R^5$ together with the carbon atoms to which they are attached form a 5- to 10-membered monocyclic or bicyclic saturated or unsaturated carbocyclic ring system which is optionally substituted with one or more of $C_1$–$C_8$ alkyl, halogen, hydroxy, and $(CH_2)_{0-2}OR^7$; and $R^4$ and $R^6$ are each independently selected from hydrogen, $C_1$–$C_{12}$ alkyl, $C_2$–$C_{12}$ alkenyl, $C_3$–$C_8$ cycloalkyl, $C_4$–$C_{20}$ alkylcycloalkyl, $C_5$–$C_8$ cycloalkenyl, $C_6$–$C_{20}$ alkylcycloalkenyl, $C_6$–$C_{10}$ aryl, $C_7$–$C_{20}$ alkylaryl, $C_8$–$C_{20}$ alkenylaryl, $C_7$–$C_{20}$ arylalkyl, heterocyclic, carboxylic acid $C_1$–$C_8$ alkyl ester, substituted $C_1$–$C_{12}$ alkyl, substituted $C_2$–$C_{12}$ alkenyl, substituted $C_3$–$C_8$ cycloalkyl, substituted $C_4$–$C_{20}$ alkylcycloalkyl, substituted $C_5$–$C_8$ cycloalkenyl, substituted $C_6$–$C_{20}$ alkylcycloalkenyl, substituted $C_6$–$C_{10}$ aryl, substituted $C_7$–$C_{20}$ alkylaryl, substituted $C_8$–$C_{20}$ alkenylaryl, substituted $C_7$–$C_{20}$ arylalkyl, substituted heterocyclic, and carboxylic acid substituted $C_1$–$C_8$ alkyl ester, wherein the substituents therefor are independently selected from halogen, hydroxy, $(CH_2)_{0-2}OR^7$, nitro, cyano, $(CH_2)_{0-2}COOR^7$, $COR^7$, $(CH_2)_{0-2}CON(R^7)_2$, and $N(R^7)_2$; or $R^3$ and $R^4$ together form one 5- to 10-membered monocyclic or bicyclic saturated or unsaturated carbocyclic ring system and $R^5$ and $R^6$ together form a second 5 to 10 membered monocyclic or bicyclic saturated or unsaturated carbocyclic ring system, wherein each ring system is optionally substituted with one or more of $C_1$–$C_8$ alkyl, halogen, hydroxy, and $(CH_2)_{0-2}OR^7$; and $R^7$ is $C_1$–$C_6$ alkyl; and $R^8$ is selected from $C_1$–$C_{20}$ hydrocarbyl and substituted $C_1$–$C_{20}$ hydrocarbyl.

38. The process according to claim 37, wherein the alkali metal carbonate is cesium carbonate.

* * * * *